United States Patent
Kurita

(10) Patent No.: US 10,609,322 B2
(45) Date of Patent: Mar. 31, 2020

(54) MEDICAL DIAGNOSTIC APPARATUS AND MEDICAL DIAGNOSTIC SYSTEM

(71) Applicant: Toshiba Medical Systems Corporation, Otawara-shi (JP)

(72) Inventor: Koichiro Kurita, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 59 days.

(21) Appl. No.: 15/605,274

(22) Filed: May 25, 2017

(65) Prior Publication Data

US 2017/0347056 A1 Nov. 30, 2017

(30) Foreign Application Priority Data

May 26, 2016 (JP) .................................. 2016-105191

(51) Int. Cl.
| | |
|---|---|
| H04N 5/445 | (2011.01) |
| H04N 7/18 | (2006.01) |
| A61B 6/00 | (2006.01) |
| A61B 8/00 | (2006.01) |
| A61B 8/08 | (2006.01) |
| G06F 19/00 | (2018.01) |
| G06T 9/00 | (2006.01) |
| H04N 5/04 | (2006.01) |

(52) U.S. Cl.
CPC ......... *H04N 5/44504* (2013.01); *A61B 6/461* (2013.01); *A61B 6/5205* (2013.01); *A61B 8/461* (2013.01); *A61B 8/5207* (2013.01); *G06F 19/321* (2013.01); *G06T 9/00* (2013.01); *H04N 5/04* (2013.01); *H04N 7/18* (2013.01)

(58) Field of Classification Search
None
See application file for complete search history.

(56) References Cited

U.S. PATENT DOCUMENTS

2009/0203973 A1* 8/2009 Donoghue .......... G06F 19/3418
600/301
2014/0022277 A1* 1/2014 Takeda ................. A61B 5/0033
345/619

(Continued)

FOREIGN PATENT DOCUMENTS

| JP | 2006-115986 | 5/2006 |
| JP | 2010-82268 | 4/2010 |

(Continued)

*Primary Examiner* — Ryan M Gray
(74) *Attorney, Agent, or Firm* — Oblon, McClelland, Maier & Neustadt, L.L.P.

(57) ABSTRACT

According to one embodiment, a medical diagnostic apparatus causes first display circuitry to display the medical image, generates a first compressed image by compressing the medical image, and wirelessly transmits the first compressed image. If marker information including position information is generated and wirelessly transmitted from the terminal device, the medical diagnostic apparatus receives the marker information. The medical diagnostic apparatus causes the first display circuitry to display a composite image in which a marker is composited on the medical image, based on the marker information. The medical diagnostic apparatus stores in storage circuitry the medical image which constitutes the composite image in accordance with a storage request.

18 Claims, 17 Drawing Sheets

(56) References Cited

U.S. PATENT DOCUMENTS

| | | | | |
|---|---|---|---|---|
| 2014/0282018 A1* | 9/2014 | Amble | ............... | G06Q 50/24 |
| | | | | 715/733 |
| 2014/0376793 A1* | 12/2014 | Lee | ............. | G06T 7/0012 |
| | | | | 382/131 |
| 2015/0005630 A1* | 1/2015 | Jung | ............. | A61B 8/565 |
| | | | | 600/437 |
| 2017/0105701 A1* | 4/2017 | Pelissier | ............. | A61B 8/4254 |

FOREIGN PATENT DOCUMENTS

| | | |
|---|---|---|
| JP | 2014-197745 | 10/2014 |
| WO | WO 2014/155853 A1 | 10/2014 |

* cited by examiner

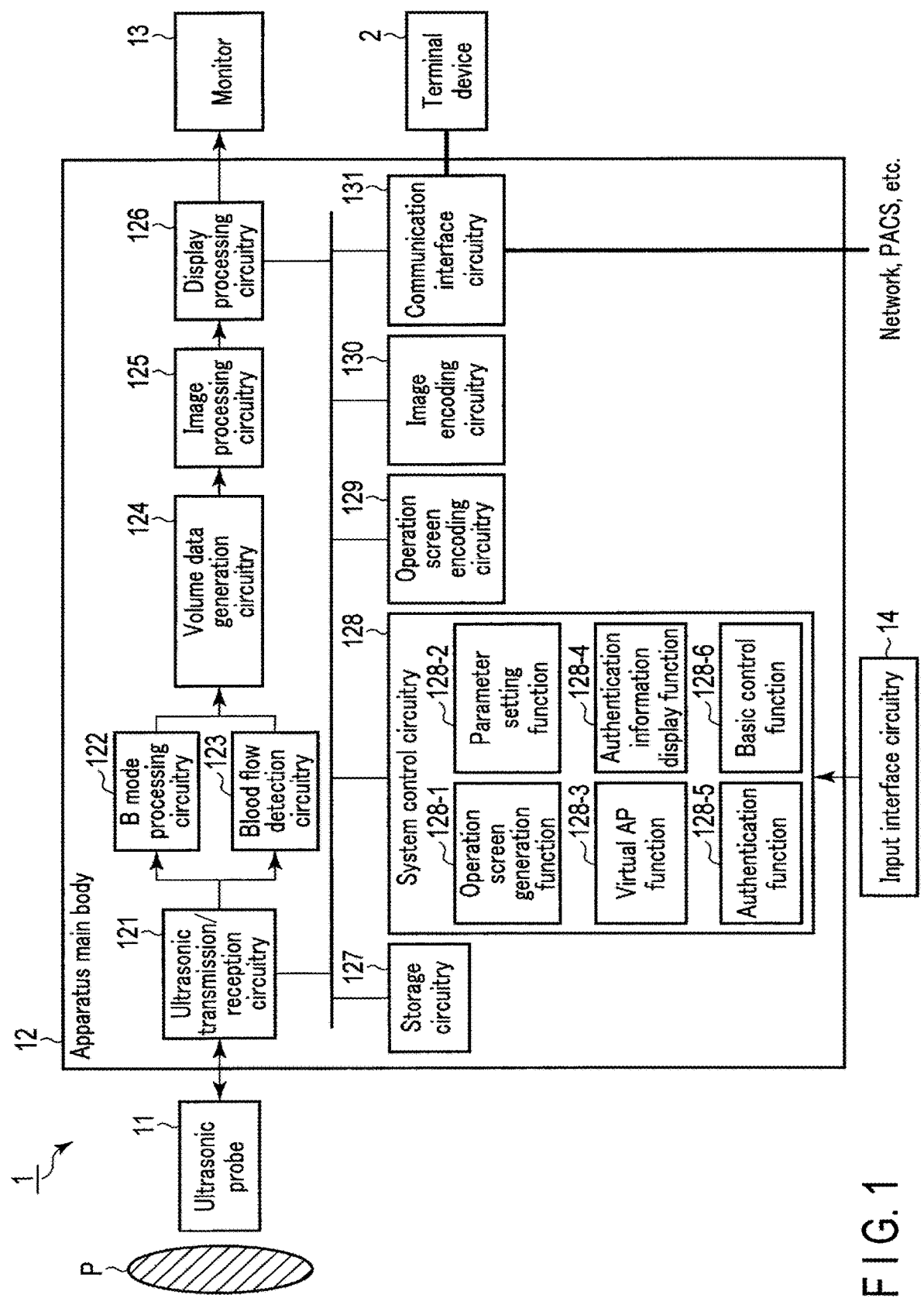
F I G. 1

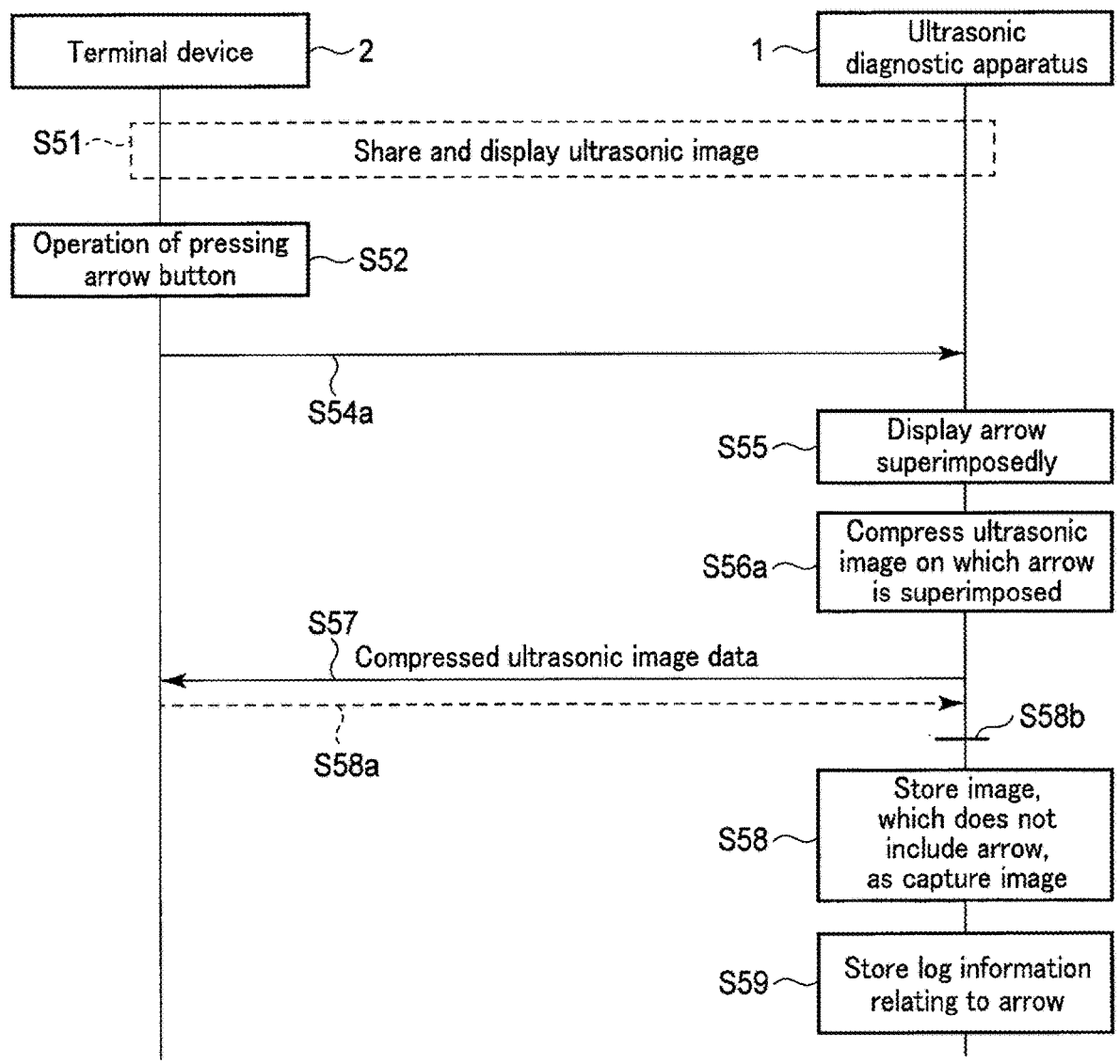
F I G. 14

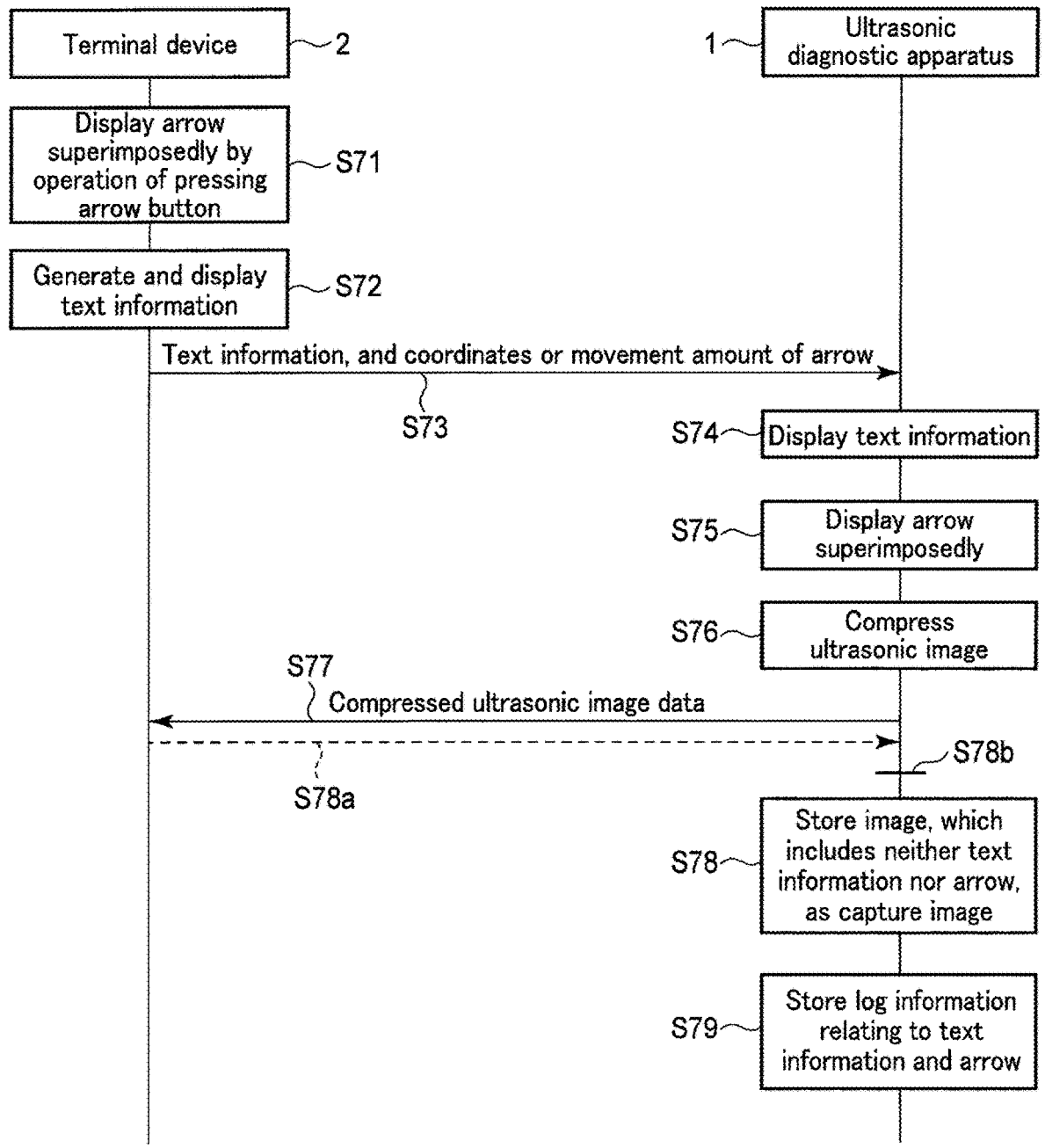
F I G. 16

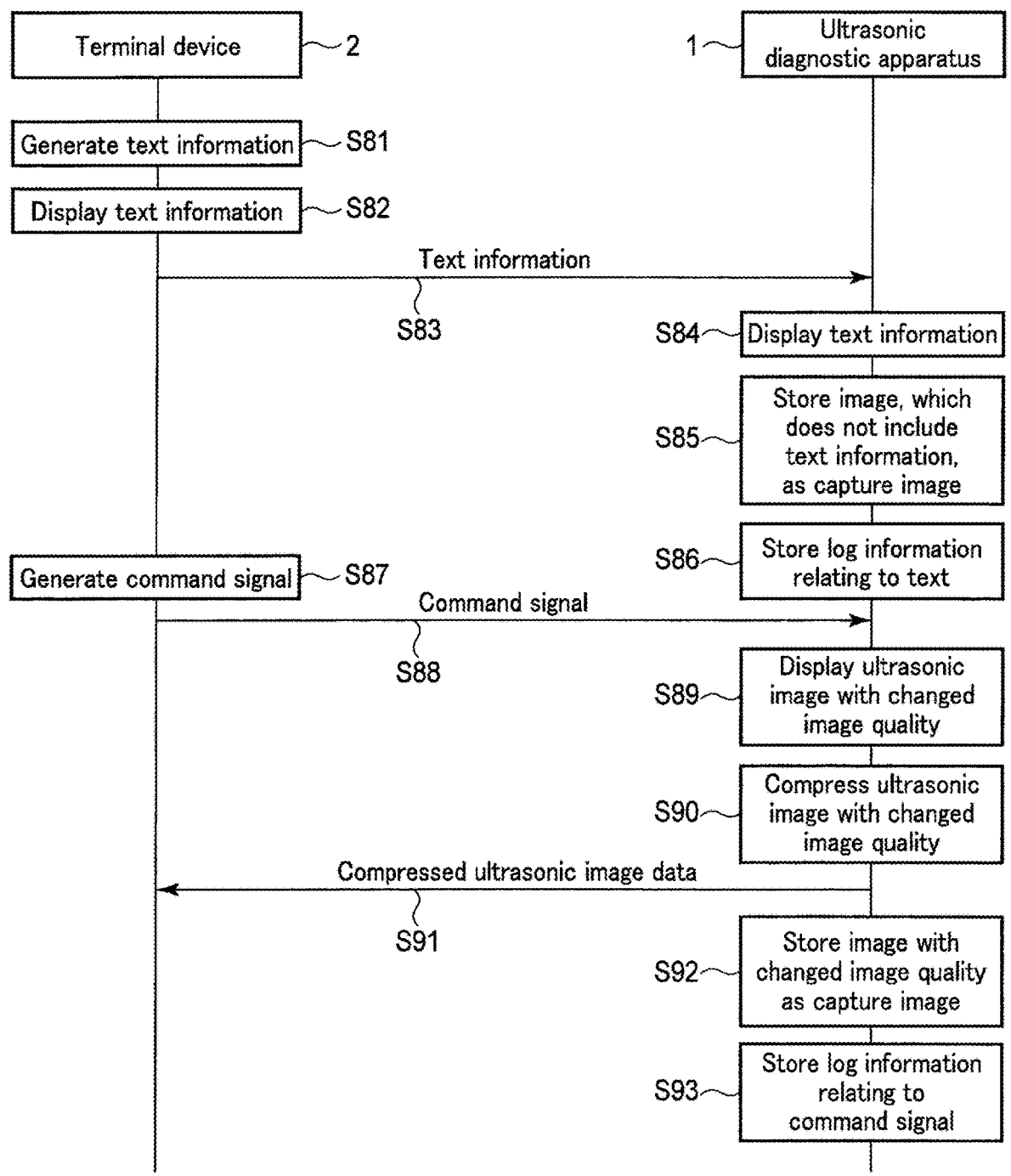
F I G. 17

MEDICAL DIAGNOSTIC APPARATUS AND MEDICAL DIAGNOSTIC SYSTEM

CROSS-REFERENCE TO RELATED APPLICATIONS

This application is based upon and claims the benefit of priority from prior Japanese Patent Application No. 2016-105191, filed on May 26, 2016, the entire contents of which are incorporated herein by reference.

FIELD

Embodiments described herein relate generally to a medical diagnostic apparatus and a medical diagnostic system.

BACKGROUND

Medical diagnostic apparatuses visualize an inside of a subject by various methods, and include various modalities such as an X-ray CT apparatus, a magnetic resonance imaging apparatus, an X-ray diagnostic apparatus, and an ultrasonic diagnostic apparatus. For example, the ultrasonic diagnostic apparatus is configured such that ultrasonic pulses, which are generated from a transducer provided in an ultrasonic probe, are radiated into a subject, and reflected ultrasonic waves, which are caused by differences between acoustic impedances of subject tissues, are received by the transducer, thereby acquiring biological information.

An operator can confirm, in real time, a motion image which is displayed on a monitor which the apparatus includes, by only performing a simple operation of putting the ultrasonic probe in contact with a body surface. In the case of an unskilled operator, he/she is accompanied by a skilled engineer or doctor, and can perform the above-described operation or confirm the motion image, while receiving proper instructions from the skilled engineer or the like.

Normally, there is no particular problem with the above-described medical diagnostic apparatus. However, according to the study by the present inventor, in the case of an unskilled operator, there is room for improvement since anxiety may be caused to the subject. For example, the situation in which the operator manipulates the ultrasonic probe while receiving instructions may cause some subjects to feel anxiety about the reliability of an examination result. In addition, in the case where the subject is a female, for example, at a time of an examination of mammary gland, there is a possibility that the presence of a skilled engineer or the like, who appears to have no relation, may cause anxiety to the subject resulting from the sense of shame.

The object is to provide a medical diagnostic apparatus and a medical diagnostic system, which enable even an unskilled operator to execute a proper operation without causing anxiety to a subject.

BRIEF DESCRIPTION OF THE DRAWINGS

FIG. 1 is a block diagram illustrating an example of a system configuration of an ultrasonic diagnostic system according to a first embodiment.

FIG. 14 is a sequence chart for describing a modification of the operation illustrated in FIG. 10.

FIG. 16 is a sequence chart for describing an operation of sharing a marker and text information.

FIG. 17 is a sequence chart for describing an operation of sharing an image with a changed image quality.

DETAILED DESCRIPTION

Figure 2:
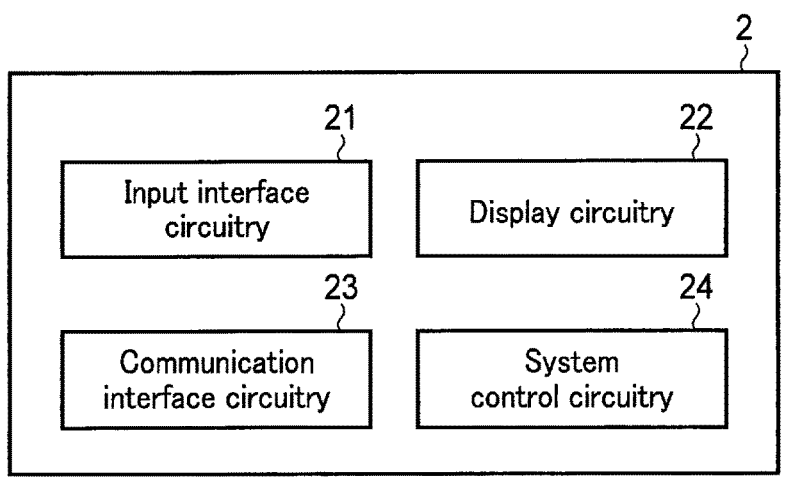
FIG. 2 is a block diagram illustrating an example of a configuration of a terminal device 2 according to the first embodiment.

In general, according to one embodiment, a medical diagnostic system includes a medical diagnostic apparatus and a terminal device.

The medical diagnostic apparatus includes medical image generation circuitry, first display control circuitry, compression circuitry, first communication circuitry, and control circuitry.

The medical image generation circuitry is configured to generate a medical image, based on an output of an ultrasonic probe or an X-ray detector.

The first display control circuitry is configured to cause first display circuitry to display the medical image.

The compression circuitry is configured to generate a first compressed image by compressing the medical image.

The first communication circuitry is configured to wirelessly transmit the first compressed image to the terminal device.

The terminal device includes second communication circuitry, second display control circuitry, and marker information generation circuitry.

The second communication circuitry is configured to receive the first compressed image which is wirelessly transmitted from the medical diagnostic apparatus.

The second display control circuitry is configured to cause second display circuitry to display the first compressed image such that the first compressed image is substantially synchronized with the display of the medical image on the first display circuitry.

The marker information generation circuitry is configured to generate marker information including position information indicative of a position on the first compressed image, in accordance with an input from a user.

Here, the second communication circuitry is configured to wirelessly transmit the marker information to the medical diagnostic apparatus.

The first communication circuitry is configured to receive the marker information which is wirelessly transmitted from the terminal device.

The first display control circuitry is configured to cause the first display circuitry to display a composite image in which a marker is composited on the medical image, based on the marker information.

The control circuitry is configured to store in storage circuitry the medical image which constitutes the composite image, in accordance with a storage request that is accepted while the composite image is being displayed on the first display circuitry.

Hereinafter, embodiments will be described with reference to the accompanying drawings. Prior to describing the embodiments, the outline of the embodiments will be described. However, the embodiments are not restricted to the mode described in this outline.

As an embodiment, in general, a medical diagnostic system including a medical diagnostic apparatus and a terminal device, which can communicate with this medical diagnostic apparatus, is first described. Then, such a mode is described that a skilled second operator supports, from the terminal device, an unskilled first operator who operates the medical diagnostic apparatus. Incidentally, the word "support" may be read as "instruct", "indicate", or "guide".

As the mode of "support", rather than a mode in which the terminal device is used as an operation console, a mode in which the terminal device is used as an input device will mainly be described. As the latter mode, for example, there is such a mode that a medical image, which is generated by the medical diagnostic apparatus, and support information, which is input in accordance with an operation of the terminal device, are shared and displayed between the medical diagnostic apparatus, which the unskilled first operator operates, and the terminal device, which the skilled second operator operates. At this time, although the skilled second operator and a subject are present in the same room, both are partitioned by a curtain or the like. Thereby, the presence of the second operator and the terminal device is not recognized by the subject. In addition, the support information is information for supporting the unskilled first operator. For example, the support information may be image data such as a marker that is superimposed and displayed on the medical image, or may be text information such as a character string that is displayed on an area different from the medical image. However, from the standpoint of preventing the support information from being recognized by the subject, speech information is not used as the support information.

In any case, when each of the medical diagnostic apparatus and the terminal device shares and displays a medical image, the support information, which is input to the terminal device, is displayed on each of the terminal device and the medical diagnostic apparatus. Accordingly, based on the support information displayed on the medical diagnostic apparatus, even an unskilled operator can execute a proper operation without causing anxiety to the subject. In addition, since support information, such as an instruction, can efficiently be transmitted to the unskilled operator, and speech information is not used as the support information, no stress is caused to the subject. The word "stress" may be read as "anxiety".

In the above-described medical diagnostic system, from the standpoint of causing no anxiety to the subject, the above-described support information is not kept in a diagnosis record of medical images, which is used for an explanation to the subject, but is kept in log information. At this time, additional information of the medical image includes time information, and the log information also includes time information. Thus, based on the time information, the support information and medical image can be associated and displayed.

The above is the outline of the embodiments. Hereinafter, in order to concretely describe the embodiments, it is assumed that the medical diagnostic apparatus according to the embodiments is an ultrasonic diagnostic apparatus which uses an ultrasonic probe as an imaging unit, among medical diagnostic apparatuses which can generate medical images based on outputs of imaging units. Incidentally, the medical diagnostic apparatus may be an X-ray diagnostic apparatus which uses an X-ray detector as an imaging unit. Alternatively, the medical diagnostic apparatus may be any one of an X-ray CT apparatus, an MRI apparatus and a nuclear medical diagnostic apparatus, which use respective detectors as imaging units.

First Embodiment

FIG. 1 is a block diagram illustrating an example of a system configuration of an ultrasonic diagnostic system according to a first embodiment. As illustrated in FIG. 1, the ultrasonic diagnostic system includes an ultrasonic diagnostic apparatus 1 and a terminal device 2. The ultrasonic diagnostic apparatus 1 and terminal device 2 are wirelessly communicably connected via a communication network. In addition, the ultrasonic diagnostic apparatus 1 is communicably connected by wire to, for example, an in-hospital network, which is different from the communication network between the ultrasonic diagnostic apparatus 1 and the terminal device 2. In this case, even if the traffic amount between the ultrasonic diagnostic apparatus 1 and the in-hospital network system increases, the communication resource, which the communication between the ultrasonic diagnostic apparatus 1 and the terminal device 2 can utilize, is not limited. In the meantime, the ultrasonic diagnostic apparatus 1 and the in-hospital network may be wirelessly communicably connected. In addition, the ultrasonic diagnostic apparatus 1 and the terminal device 2 may be communicably connected by wire. In each case of the wire and wireless communications, it is preferable that the communication between the ultrasonic diagnostic apparatus 1 and the terminal device 2 is executed directly without intervention of an external server, from the standpoint of substantially synchronizing the image display.

The ultrasonic diagnostic apparatus 1 includes an ultrasonic probe 11, an apparatus main body 12, a monitor 13 and input interface circuitry 14. The apparatus main body 12 and terminal device 2 are communicably connected via a communication network.

The ultrasonic probe 11 is a device (probe) which transmits ultrasonic waves to a subject which is typically a living body, and receives reflected waves from the subject, which are based on the transmitted ultrasonic waves. The ultrasonic probe 11 includes a plurality of piezoelectric transducers (ultrasonic transducers) which are arrayed at a distal end thereof, a matching layer, and a backing material. The ultrasonic probe 11 is a one-dimensional array probe in which the ultrasonic transducers are arrayed in a predetermined direction.

The piezoelectric transducers transmit ultrasonic waves in a desired direction in a scan region, based on a driving signal from ultrasonic transmission/reception circuitry 121 (to be described later), and receive reflected waves from the subject. The piezoelectric transducers convert the received reflected waves to an electric signal. The matching layer is an intermediate layer which is provided on the piezoelectric transducers, thereby efficiently propagating ultrasonic energy. The backing material is provided on a side opposite to the matching layer such that the piezoelectric transducers are sandwiched between the matching layer and the backing material, and the backing material prevents propagation of ultrasonic waves to the rear side from the piezoelectric transducers.

If ultrasonic waves are transmitted from the ultrasonic probe 11 to the subject, the transmitted ultrasonic waves are successively reflected by discontinuous planes of acoustic impedances of subject tissues, and are received by the ultrasonic probe 11 as an echo signal. The amplitude of this echo signal depends on a difference between the acoustic impedances at the discontinuous planes at which the reflection occurs. In addition, an echo in a case in which transmitted ultrasonic pulses are reflected by a moving blood flow undergoes a frequency shift, depending on a velocity component in an ultrasonic transmission/reception direction of a moving body by a Doppler effect.

Incidentally, in the present embodiment, it is assumed that the ultrasonic probe 11 is the one-dimensional array probe. However, aside from this example, the ultrasonic probe 11 may be, as a probe capable of acquiring volume data, a two-dimensional array probe (a probe in which a plurality of ultrasonic transducers are arrayed in a two-dimensional matrix) or a mechanical 4D probe (a probe capable of executing ultrasonic scan while mechanically swinging an ultrasonic transducer array in a direction perpendicular to the direction of the array). This ultrasonic probe 11 constitutes an imaging unit.

The apparatus main body 12 includes ultrasonic transmission/reception circuitry 121, B mode processing circuitry 122, blood flow detection circuitry 123, volume data generation circuitry 124, image processing circuitry 125, display processing circuitry 126, storage circuitry 127, system control circuitry 128, operation screen encoding circuitry 129, image encoding circuitry 130, and communication interface circuitry 131. The ultrasonic transmission/reception circuitry 121, display processing circuitry 126, storage circuitry 127, system control circuitry 128, operation screen encoding circuitry 129, image encoding circuitry 130, and communication interface circuitry 131 are mutually connected via a bus.

The ultrasonic transmission/reception circuitry 121 includes trigger generation circuitry, delay circuitry and pulser circuitry, which are not shown. The trigger generation circuitry repeatedly generates trigger pulses for forming transmission ultrasonic waves at a predetermined rate frequency fr [Hz] (cycle; 1/fr [second]). In addition, the delay circuitry imparts to each trigger pulse a delay time which is necessary for converging ultrasonic waves into a beam on a channel-by-channel basis, and for determining transmission directivity. The pulser circuitry applies a driving pulse to the ultrasonic probe 11 at a timing based on the trigger pulse.

In addition, the ultrasonic transmission/reception circuitry 121 includes amplifier circuitry, an A/D converter, delay circuitry and an adder, which are not shown. The amplifier circuitry amplifies, on a channel-by-channel basis, an echo signal which is taken in via the ultrasonic probe 11. The A/D converter converts the amplified analog echo signal to a digital echo signal. The delay circuitry imparts to the A/D converted echo signal a delay time which is necessary for determining reception directivity and for executing reception dynamic focusing. Thereafter, the adder executes a process of adding digital echo signals of respective channels, to which the delay time has been imparted, and the phases of which have been uniformized. By this addition, a reflected component from the direction corresponding to the reception directivity of the echo signal is emphasized, and a comprehensive beam of ultrasonic transmission/reception is formed by the reception directivity and transmission directivity.

The B mode processing circuitry 122 is a processor which generates a plurality of B mode data, based on the echo signal received from the ultrasonic transmission/reception circuitry 121. The B mode processing circuitry 122 receives the echo signal from the ultrasonic transmission/reception circuitry 121, subjects the received echo signal to logarithmic amplification, an envelope detection process, etc., and generates a plurality of B mode data in which a signal strength is expressed by the magnitude of brightness. The generated plural B mode data are stored in a RAW data memory (not shown) as B mode RAW data which are B mode data on three-dimensional ultrasonic scanning lines.

The blood flow detection circuitry 123 is a processor which generates a plurality of blood flow data, based on the echo signal received from the ultrasonic transmission/reception circuitry 121. The blood flow detection circuitry 123 extracts a blood flow signal from the echo signal received from the ultrasonic transmission/reception circuitry 121, and generates a plurality of blood flow data. The generated plural blood flow data are stored in a RAW data memory (not shown) as blood flow RAW data which are blood flow data on three-dimensional ultrasonic scanning lines. The extraction of the blood flow is normally executed by CFM (Color Flow Mapping). In this case, the blood flow signal is analyzed, and blood flow information, such as an average velocity, variance and power, is calculated at multiple points as the blood flow data.

The volume data generation circuitry 124 is a processor which generates volume data, based on the RAW data stored in the RAW data memory.

The volume data generation circuitry 124 generates B mode volume data by executing RAW-voxel conversion, which includes an interpolation process with the addition of spatial position information, on the B mode RAW data stored in the RAW data memory.

The volume data generation circuitry 124 generates blood flow volume data by executing RAW-voxel conversion, which includes an interpolation process with the addition of spatial position information, on the blood flow RAW data stored in the RAW data memory.

The image processing circuitry 125 is a processor which generates various kinds of image data, based on the volume data received from the volume data generation circuitry 124. The image processing circuitry 125 executes predetermined image processes, such as volume rendering, MPR (Multi- Planar Reconstruction) and MIP (Maximum Intensity Projection), on the volume data received from the volume data generation circuitry 124. In the meantime, in order to reduce noise and to improve the connection between images, a two-dimensional filter may be inserted after the image processing circuitry 125, thereby performing spatial smoothing.

The above-described ultrasonic transmission/reception circuitry 121, B mode processing circuitry 122, blood flow detection circuitry 123, volume data generation circuitry 124 and image processing circuitry 125 constitute medical image generation circuitry which generates a medical image, based on the output of the ultrasonic probe 11 which functions as the imaging unit.

The display processing circuitry 126 is a processor which generates ultrasonic image data relating to an ultrasonic image which is to be displayed on the monitor 13, based on the various image data generated and processed in the image processing circuitry 125. The display processing circuitry 126 executes various processes, such as dynamic range, brightness, contrast and γ curve correction, and RGB conversion, on the various image data generated and processed in the image processing circuitry 125. The display processing circuitry 126 generates the ultrasonic image data relating to the ultrasonic image which is to be displayed on the monitor 13, based on a preset resolution and display frame rate. The display frame rate is, for example, the number of display frames of ultrasonic images, which are generated per second by the display processing circuitry 126. Incidentally, the display frame rate is basically equal to an acoustic frame rate which is determined by a scan cycle for a subject with use of an ultrasonic probe in usual cases. Incidentally, a fixed value, for instance, 30 frames per second, may be set as the display frame rate.

This display processing circuitry 126 constitutes first display control circuitry which causes the monitor 13 that functions as first display circuitry to display the medical image which is generated by the medical image generation circuitry, in accordance with the control from the system control circuitry 128. In addition, the display processing circuitry 126 may display a marker on the medical image, based on marker information received from the terminal device 2, in accordance with the control from the system control circuitry 128. Specifically, the display processing circuitry 126 may cause the monitor 13 to display a composite image in which a marker is composited on the medical image. Incidentally, the expression "to display a marker on a medical image" and the expression "to display a composite image in which a marker is composited on a medical image" may be read interchangeably, as needed. In addition, in accordance with the control from the system control circuitry 128, the display processing circuitry 126 may cause the monitor 13 to display, together with the medical image, text information which is received from the terminal device 2, and may display a marker on the medical image, based on marker information which is received from the terminal device 2. Specifically, the display processing circuitry 126 may cause the monitor 13 to display the text image, together with the composite image in which the marker is composited on the medical image. At this time, it is preferable that the display processing circuitry 126 displays the text information at that position of the monitor 13, which does not overlap the medical image. Besides, the display processing circuitry 126 may display a marker on the medical image, based on the marker information, and may display a trace of the marker on the medical image for a predetermined time. Specifically, the display processing circuitry 126 may display a composite image in which a marker is composited on the medical image, based on the marker information, and may display the trace of the marker in this composite image for a predetermined time. Furthermore, the display processing circuitry 126 may specify a medical image and marker information in the storage circuitry 127, based on time information designated by the user, and may display a composite image in which a marker is composited on the specified medical image, based on the specified marker information. In addition, in accordance with the control of the system control circuitry 128, the display processing circuitry 126 may cause the monitor 13 to display the text information in the storage circuitry 127 together with the medical image, based on the time information designated by the user, and may display the marker on the medical image, based on the marker information in the storage circuitry 127. Besides, in accordance with the control of the system control circuitry 128, the display processing circuitry 126 may cause the monitor 13 to display the text information in the storage circuitry 127 together with a capture image, based on the time information designated by the user. Moreover, for example, upon receiving from the terminal device 2 a command signal for changing the image quality of the medical image, the display processing circuitry 126 may change the image quality of the medical image which is being displayed on the monitor 13. In this case, for example, there may be such a situation that, after both the text information to the effect that the image quality of the medical image is to be changed, and the medical image, were displayed on the monitor 13 prior to the reception of the command signal, the command signal is wirelessly transmitted from the terminal device 2.

The storage circuitry 127 includes a storage medium or the like which can be read by a processor, such as a magnetic or optical storage medium or a semiconductor memory. The storage circuitry 127 stores programs for realizing an operation screen generation function 128-1, a parameter setting function 128-2, a Software AP function 128-3, an authentication information display function 128-4, an authentication function 128-5 and a basic control function 128-6; diagnosis protocols; a data size per 1 frame of an ultrasonic image and a display frame rate at a time of generating ultrasonic image data; a transmission/reception condition, such as a compression ratio of ultrasonic image data, at a time of transferring ultrasonic image data from the ultrasonic diagnostic apparatus 1 to terminal device 2; and other data groups. Incidentally, the compression ratio is preset to a predetermined value.

In addition, the storage circuitry 127 stores a terminal display frame rate. The terminal display frame rate is the number of display frames per second of ultrasonic images that are displayed on a display which display circuitry 22 of the terminal device 2 includes. Incidentally, the terminal display frame rate is basically equal to the display frame rate.

Besides, the storage circuitry 127 stores an operation screen database. The operation screen database is a set of data which treats, as one logic record, image data and additional information of this image data, the image data representing an operation screen which is displayed on a touch panel that input interface circuitry 21 of the terminal device 2 (to be described later) includes, and through which a second operator 4 operates the ultrasonic diagnostic apparatus 1 from the terminal device 2.

The image data representing the operation screen includes image data of various patterns which are necessary for the second operator 4 to operate the ultrasonic diagnostic apparatus 1 from the terminal device 2. The image data representing the operation screen includes graphic data for accepting an operation from the second operator 4. In addition, the image data representing the operation screen includes image data representing at least one function button which is disposed on the operation screen. The image data representing the function button is image data for discriminating which function is executed by the button on the touch panel which the input interface circuitry 21 of the terminal device 2 includes.

The additional information of the image data is information indicating which function is executed, for example, when an area of coordinates, where a predetermined function button is disposed, is pressed on the operation screen represented by the image data. Specifically, the additional information of the image data includes, for example, function information of executing a predetermined process, and position information indicating where a button corresponding to this function is disposed on the operation screen. The additional information of the image data is, for instance, additional information of various patterns corresponding to the image data representing the operation screen. As will be described later, the additional information of the image data is utilized when system control circuitry 24 of the terminal device 2 generates a command signal.

In addition, the storage circuitry 127 stores identification information which is necessary at a time of confirming whether a person who operates the ultrasonic diagnostic apparatus 1 from the terminal device 2 has the right of the operation, in the authentication function 128-5 of the system control circuitry 128 (to be described later). The identification information is, for example, a password or the like. Incidentally, the password may be manually set in the ultrasonic diagnostic apparatus 1, or may be generated automatically. In addition, the password may be acquired from a predetermined external apparatus.

The system control circuitry 128 is, for example, a processor which controls each structural circuitry of the ultrasonic diagnostic apparatus 1. The system control circuitry 128 functions as a central unit of the ultrasonic diagnostic apparatus 1. The system control circuitry 128 calls respective operation programs from the storage circuitry 127 and executes the called programs, thereby realizing the operation screen generation function 128-1, parameter setting function 128-2, Software AP function 128-3, authentication information display function 128-4, authentication function 128-5 and basic control function 128-6.

The operation screen generation function 128-1 is a function of generating operation screen data which is transmitted to the terminal device 2. Specifically, in the operation screen generation function 128-1, the system control circuitry 128 receives a command signal from the terminal device 2 via the communication interface circuitry 131. The command signal is a signal for instructing a change to a predetermined operation screen from an operation screen which is displayed on the touch panel which the input interface circuitry 21 of the terminal device 2 (to be described later) includes. The command signal includes information showing the operation screen after the change. In the meantime, as will be described later, if the second operator 4 presses a predetermined button on the touch panel which the input interface circuitry 21 of the terminal device 2 includes, the system control circuitry 24 of the terminal device 2 refers to additional information of the image data which represents the pressed predetermined button, and generates a command signal corresponding to the additional information.

In addition, from the operation screen database prestored in the storage circuitry 127, the system control circuitry 128 acquires, as terminal operation screen data, image data corresponding to the operation screen after the change, which the received command signal requests, and additional information of this image data.

Examples of the operation screen after the change, which the received command signal requests, include an initial screen immediately after the screen displaying the ultrasonic image has been switched to an operation screen for operating various functions; an operation screen for operating a predetermined function, which is different from the initial screen; and an operation screen on which a predetermined function button in the operation screen is highlight-displayed.

In the meantime, the system control circuitry 128 may slightly correct the acquired terminal operation screen data in accordance with the screen specifications of the terminal device 2.

The system control circuitry 128 sends the acquired terminal operation screen data to the operation screen encoding circuitry 129 (to be described later).

The parameter setting function 128-2 is a function of setting parameters of ultrasonic image data which is transmitted from the ultrasonic diagnostic apparatus 1 to the terminal device 2.

Specifically, in the parameter setting function 128-2, the system control circuitry 128 acquires from the storage circuitry 127 a data size per 1 frame of a predetermined ultrasonic image which is generated by the display processing circuitry 126 of the ultrasonic diagnostic apparatus 1, a display frame rate and a preset compression ratio of ultrasonic image data, while the ultrasonic image data generated by the display processing circuitry 126 is being displayed on the monitor 13. The system control circuitry 128 calculates an image data generation rate Ru, for example, based on the acquired data size per 1 frame of the predetermined ultrasonic image, display frame rate and preset compression ratio of ultrasonic image data.

In addition, the system control circuitry 128 measures an image data transfer rate Rt of the communication network between the ultrasonic diagnostic apparatus 1 and the terminal device 2. The image data transfer rate Rt is an effective transfer bit rate which is usable for data transfer in the communication network between the ultrasonic diagnostic apparatus 1 and the terminal device 2. The system control circuitry 128 compares the calculated image data generation rate Ru and the measured image data transfer rate Rt. As a result of the comparison, if Ru is greater than Rt, the system control circuitry 128 changes the preset value, for example, so that the Ru after compression becomes equal to Rt, that is, so that the compression ratio at a time of compression processing of ultrasonic image data in the image encoding circuitry 130 (to be described later) becomes higher. Incidentally, to change the preset value so that the compression ratio becomes higher means to make smaller the data size of the compressed data at a compression ratio after the change. In addition, if the result of the comparison indicates that Ru is not greater than Rt, the system control circuitry 128 does not change the compression ratio, and keeps the preset compression ratio.

In the meantime, in the above description, the system control circuitry 128 controls only the compression ratio. However, for example, as will be described later, large-capacity DICOM (Digital Imaging and COmmunication in Medicine) data or the like is transferred between the ultrasonic diagnostic apparatus 1 and a network system such as PACS. Thus, there is a case in which the real-time performance of ultrasonic image data transmission from the ultrasonic diagnostic apparatus 1 to the terminal device 2 cannot sufficiently be secured by the control of only the compression ratio. In such a case, the terminal display frame rate is controlled in addition to the control of the compression ratio or in place of the control of the compression ratio. Specifically, the system control circuitry 128 executes the parameter setting function 128-2, and calculates an image data generation rate Rum, based on the data size per 1 frame of the ultrasonic image, the display frame rate and a high compression ratio corresponding to a tolerable limit value of ultrasonic image data, which are acquired from the storage circuitry 127. The high compression ratio corresponding to the tolerable limit value means a highest compression ratio which is set according to a lowest image quality that is tolerable, for example, with respect to a predetermined ultrasonic image. In addition, the system control circuitry 128 compares the calculated image data generation rate Rum and the measured image data transfer rate Rt. If the comparison result indicates that Rum is not greater than Rt, the system control circuitry 128 changes the preset value, for example, so that the Ru after compression becomes equal to Rt, that is, so that the compression ratio at a time of compression processing of ultrasonic image data in the image encoding circuitry 130 (to be described later) becomes higher. In addition, if the comparison result indicates that Rum is greater than Rt, the system control circuitry 128 sets, for example, the compression ratio at a time of compression processing of ultrasonic image data in the image encoding circuitry 130 (to be described later) to the tolerable limit value. Besides, if the comparison result indicates that Rum is greater than Rt, the system control circuitry 128 makes, for example, the terminal display frame rate lower than a preset value, in addition to the setting of the compression ratio.

Besides, the system control circuitry 128 may execute parameter setting so that, for example, the display processing circuitry 126 cuts a part of the ultrasonic image generated by the display processing circuitry 126, in place of the control of the compression ratio and terminal display frame rate, or in addition to the control of the compression ratio and terminal display frame rate.

The Software AP function 128-3 is a function of generating a virtual access point for the terminal device 2 to wirelessly communicate with the ultrasonic diagnostic apparatus 1. Specifically, in the Software AP function 128-3, if a second console start button is pressed, the system control circuitry 128 controls the communication interface circuitry 131 and generates a virtual access point. The second console start button is provided at a predetermined position on the touch panel which the input interface circuitry 14 of the ultrasonic diagnostic apparatus 1 (to be described later) includes. Incidentally, the second console start button may be provided as one of plural switch buttons that are provided in a panel switch which the input interface circuitry 14 (to be described later) includes.

In addition, at the time of generating the access point, the system control circuitry 128 sets an SSID (Service Set Identifier) and a password. The SSID and password may be manually set by being input by the first operator 3 or second operator 4 via the input interface circuitry 14, or may be automatically set. In the meantime, the password is a one-time password which is updated at each time of communication connection between the ultrasonic diagnostic apparatus 1 and terminal device 2, or is updated periodically. The one-time password is a password which is generated, for example, based on a mathematical algorithm or the like.

In addition, the system control circuitry 128 is communicably connected to the terminal device 2 via the communication interface circuitry 131, based on preset connection information. In the meantime, in the present embodiment, the authentication relating to the communication connection between the ultrasonic diagnostic apparatus 1 and terminal device 2 is automatically executed based on preset connection information. The preset connection information is information that is necessary for communication connection, such as the SSID of the generated access point, the password necessary for the connection, and MAC addresses (Media Access Control addresses) of the ultrasonic diagnostic apparatus 1 and terminal device 2.

Incidentally, the system control circuitry 128 may establish the communication connection after receiving a communication connection request from the terminal device 2. In this case, the authentication process is executed by determining, on the ultrasonic diagnostic apparatus 1 side, whether the password or the like that is input in the terminal device 2 is correct or not. For example, the communication between the ultrasonic diagnostic apparatus 1 and terminal device 2 may be permitted when the password, which is displayed at a predetermined position on the screen of the monitor 13, was input in the terminal device 2.

Besides, after the establishment of the communication connection to the terminal device 2, the system control circuitry 128 requests the terminal device 2 via the communication interface circuitry 131 to input the password for operating the ultrasonic diagnostic apparatus 1 from the terminal device 2.

The authentication information display function 128-4 is a function of presenting identification information which is necessary for the terminal device 2 to operate the ultrasonic diagnostic apparatus 1. Specifically, in the authentication information display function 128-4, the system control circuitry 128 displays identification information on the monitor 13. The identification information is, for example, the SSID and password which are set by the Software AP function 128-3. Of the identification information, the password is a string of characters, signs and numerals, which are preset in order to authenticate whether the second operator 4 is an authentic user who directly executes a predetermined operation relating to the ultrasonic diagnostic apparatus 1 by the terminal device 2. This password may be different from the password which was set by the Software AP function 128-3. In this case, the password is a one-time password which is updated at each time of communication connection between the ultrasonic diagnostic apparatus 1 and terminal device 2, or is updated periodically. Incidentally, although the password has been described by way of example as the identification information which is necessary for authentication, a predetermined ID, which is different from the SSID, and a password may be used as the identification information.

The authentication function 128-5 is a function of executing authentication of response data, when the response data is sent from the terminal device 2 to the ultrasonic diagnostic apparatus 1 in accordance with a request for password input after the password input was requested from the Software AP function 128-3 to the terminal device 2, and of permitting a predetermined operation relating to the ultrasonic diagnostic apparatus 1. Specifically, in the authentication function 128-5, the system control circuitry 128 receives, via the communication interface circuitry 131, response data to the request for password input from the terminal device 2. The system control circuitry 128 compares a password, which is included in the received response data, with the password displayed by the authentication information display function 128-4. If the password included in the response data agrees with the password displayed by the authentication information display function 128-4, the system control circuitry 128 permits the second operator 4 to directly execute a predetermined operation relating to the ultrasonic diagnostic apparatus 1 from the terminal device 2. The authentication function 128-5 constitutes, for example, authentication circuitry which permits communication between the communication interface circuitry 131 and the terminal device 2, when the password displayed at a predetermined position on the screen of the monitor 13 has been input by the terminal device 2.

The basic control function 128-6 is a function of controlling basic operations such as an input/output of the ultrasonic diagnostic apparatus 1. Specifically, in the basic control function 128-6, the system control circuitry 128 receives a command signal, for example, via the input interface circuitry 14. The command signal is a signal which instructs the ultrasonic diagnostic apparatus 1 to execute a predetermined function. The command signal includes a predetermined execution command. When the command signal is indicative of a predetermined command for operating predetermined circuitry of the ultrasonic diagnostic apparatus 1, the system control circuitry 128 controls the predetermined circuitry in accordance with the purpose of the predetermined command. In addition, the system control circuitry 128 displays, via the display processing circuitry 126, the ultrasonic diagnosis image and operation screen on the monitor 13.

In addition, the basic control function 128-6 of the system control circuitry 128 controls operations corresponding to capture image generation circuitry, medical image storing circuitry, log storing circuitry, and capture image storing circuitry. When both the text information and the medical image are displayed on the monitor 13 which functions as the first display circuitry, the capture image generation circuitry generates a capture image which does not include the text information with respect to the information in the screen of the monitor 13. Here, the capture image is an image of a storage target in the displayed screen. The capture image is obtained, for example, by excluding unnecessary information from the displayed screen. Alternatively, the capture image is obtained by extracting an image of a storage target from the displayed screen. For example, when a screen, in which a first area including a storage-target image and a second area including an unnecessary image are juxtaposed, is displayed, the capture image is obtained by extracting the storage-target image of the first area from the screen. In addition, for example, when a composite image, in which a first layer including a storage-target image and a second layer including unnecessary information are superimposed and composited, is displayed, the capture image is obtained by extracting the storage-target image of the first layer from the composite image. Incidentally, the term "capture image" may be read, as needed, as a term "image" which does not use the expression "capture", such as "image for storage" or "medical image for storage". When a composite image, in which a marker is composited on a medical image, is displayed, the medical image storing circuitry stores, in the storage circuitry 127, the medical image which constitute the composite image, and time information by associating the medical image and the time information, in accordance with a storage request which is accepted by the terminal device 2 or input interface circuitry 14. Specifically, for example, the medical image storing circuitry stores the medical image in the storage circuitry 127 in accordance with a control signal corresponding to the storage request. Incidentally, the medical image, which constitutes the composite image, is a medical image which does not include a marker. When text information, a medical image and a marker are displayed on the monitor 13, the log storing circuitry stores in the storage circuitry 127 log information including the text information, marker information and time information. In addition, when both the text information and the medical image are displayed on the monitor 13, the log storing circuitry stores in the storage circuitry 127 log information including the text information and time information. The capture image storing circuitry stores, in the storage circuitry 127, the capture image and time information by associating the capture image and time information, in accordance with a storage request which is accepted by the terminal device 2 or input interface circuitry 14. Specifically, for example, the capture image storing circuitry stores the capture image in the storage circuitry 127 in accordance with a control signal corresponding to the storage request.

The operation screen encoding circuitry 129 is a processor which compresses terminal operation screen data which is acquired by the operation screen generation function 128-1 of the system control circuitry 128, in accordance with the control of the system control circuitry 128. In the meantime, since it is rare that the entirety of the operation screen constantly varies along the time axis, it is preferable that the operation screen encoding circuitry 129 employs a compression technique such as MPEG (Moving Picture Experts Group) which compresses an information amount by taking a difference between image data which neighbor on the time axis. In addition, it is preferable that the operation screen encoding circuitry 129 employs a compression technique such as MPEG which compresses an information amount by taking a difference between additional information pieces of image data which neighbor on the time axis. In this case, a frame includes image data, and additional information of this image data.

The image encoding circuitry 130 is a processor which compresses the ultrasonic image data which is generated by the display processing circuitry 126, in accordance with the control of the system control circuitry 128. Incidentally, since it is necessary to display an ultrasonic image which is a constantly new image with respect to the time axis, it is preferable to use a compression technique, such as JPEG (Joint Photographic Expert Group), by which a high compression ratio can be obtained.

The communication interface circuitry 131 is a processor which controls, via the communication network, a communication connection to the terminal device 2, and various data communications. The communication interface circuitry 131 includes a built-in wireless LAN antenna. The communication interface circuitry 131 transmits the terminal operation screen, which is compressed by the operation screen encoding circuitry 129, to the terminal device 2 via the communication network in accordance with the control of the system control circuitry 128. The communication interface circuitry 131 transmits the image data, which is compressed by the image encoding circuitry 130, to the terminal device 2 via the communication network in accordance with the control of the system control circuitry 128. Besides, the communication interface circuitry 131 receives, via the communication network, a command signal which is transmitted from the terminal device 2, in accordance with the control of the system control circuitry 128. Furthermore, the communication interface circuitry 131 receives, via the communication network, a control signal which is transmitted from the terminal device 2, in accordance with the control of the system control circuitry 128.

This communication interface circuitry 131 constitutes first communication circuitry which wirelessly transmits to the terminal device 2 the compressed image which is generated by the image encoding circuitry 130 that functions as compression circuitry, and receives the text information and marker information which are wirelessly transmitted from the terminal device 2.

Here, the compressed image is an image, the data amount of which has been made smaller than the data amount of the image before compression, in order to reduce the load of wireless communication. The compressed image may be generated by lossless compression or lossy compression. When the data amount of the image before compression is d1, the data amount of the compressed image is d2, and the compression ratio is ρ [%], the relationship expressed by the following equation is established:

$$\rho = d2/d1 \times 100 \ [\%]$$

Incidentally, in usual cases, the compressed image and the above-described capture image are different images. The reason for this is that, in usual cases, the capture image is an image before compression. However, when an image after compression may be stored, such as when the compression ratio is low or lossless compression is executed, the compressed image may be used as the capture image.

In addition, when the text information and marker information are individually wirelessly transmitted from the terminal device 2, the communication interface circuitry 131 receives the text information and marker information individually. Besides, there is a case in which, after the communication interface circuitry 131 received text information and both the text information and medical image were displayed on the monitor 13, the communication interface circuitry 131 receives the command signal which is wirelessly transmitted from the terminal device 2. This case corresponds to, for example, a case in which text information to the effect that an image quality parameter is to be changed, and a command signal for changing the image quality parameter, are successively wirelessly transmitted from the terminal device 2. In addition, there is a case in which the communication interface circuitry 131 receives a control signal which is wirelessly transmitted from the terminal device 2. This case corresponds to, for example, a case in which a control signal corresponding to a storage request for an image of a storage target, among displayed images, is wirelessly transmitted from the terminal device 2. Examples of the image of the storage target include a medical image which constitutes a composite image, and a capture image which does not include text information.

The input interface circuitry 14 includes a trackball, a panel switch, a mouse, a keyboard, a touch pad for executing an input operation by touching an operation surface, and a touch panel, which are used in order to take in the apparatus main body 12 various instructions from the first operator 3, conditions, a region-of-interest (ROI) setting instruction, various image quality condition setting instructions, etc. The panel switch is a physical switch which is disposed on the ultrasonic diagnostic apparatus 1. The touch panel is a panel in which the display screen of the monitor 13 and the touch pad are integrated. The input interface circuitry 14 is connected to the system control circuitry 128 of the apparatus main body 12, and converts an input operation, which is received from the operator, to an electric signal, and outputs the electric signal to the control circuitry. Incidentally, in the present specification, the input interface circuitry 14 is not limited to circuitry including physical operational components such as a mouse and a keyboard. For instance, examples of the input interface circuitry include electric signal processing circuitry which receives an electric signal corresponding to an input operation from an external input device provided separately from the apparatus, and outputs this electric signal to the system control circuitry 128 of the apparatus main body 12. This input interface circuitry 14 constitutes, for example, input circuitry which, upon accepting an input of a storage request in accordance with a user's operation, sends a control signal to the system control circuitry 128 in accordance with the accepted storage request.

The terminal device 2 is a device which is communicably connected to the ultrasonic diagnostic apparatus 1 via a communication network R, and is usable at a distance from the ultrasonic diagnostic apparatus 1. The terminal device 2 may be, for example, a tablet-type information terminal, a PC (Personal Computer) or the like. In the present embodiment, a tablet-type information terminal is illustrated as an example of the terminal device 2.

FIG. 2 is a block diagram illustrating an example of the configuration of the terminal device 2 according to the first embodiment. As illustrated in FIG. 2, the terminal device 2 includes input interface circuitry 21, display circuitry 22, communication interface circuitry 23, and system control circuitry 24.

The input interface circuitry 21 may be, for instance, a touch panel which is stacked on a display screen of a display that the display circuitry 22 includes. The input interface circuitry 21 accepts an operation instruction from the second operator 4, and outputs the operation instruction to the system control circuitry 24. This input interface circuitry 21 constitutes, for example, input circuitry which, upon accepting an input of a storage request in accordance with the user's operation, sends a control signal to the communication interface circuitry 23 in accordance with the accepted storage request. Incidentally, when a keyboard is attached to the main body of the tablet-type terminal device 2, the input interface circuitry 21 further includes this keyboard.

The display circuitry 22 includes a general display output device, such as a liquid crystal display or an OLED (Organic Light Emitting Diode) display. In accordance with the control of the system control circuitry 24, the display circuitry 22 displays an operation screen for operating the ultrasonic diagnostic apparatus 1, and various images.

The communication interface circuitry 23 is a processor which is communicably connected to the ultrasonic diagnostic apparatus 1 via the communication network, and transmits and receives data, in accordance with the control of the system control circuitry 24. The communication interface circuitry 23 constitutes, for example, second communication circuitry which receives a compressed image that is wirelessly transmitted from the ultrasonic diagnostic apparatus 1 that functions as the medical diagnostic apparatus, and wirelessly transmits text information and marker information, which includes position information of a marker displayed on the compressed image, to the ultrasonic diagnostic apparatus 1. In addition, the communication interface circuitry 23 may wirelessly transmit a control signal, which is sent from the input interface circuitry 21, to the ultrasonic diagnostic apparatus 1. The communication interface circuitry 23 may wirelessly transmit the text information and marker information individually to the ultrasonic diagnostic apparatus 1. Besides, as the position information of the marker, for example, use can be made of the coordinates or the movement amount of the marker.

The system control circuitry 24 is, for example, a processor which controls each structural circuitry of the terminal device 2. The system control circuitry 24 functions as a central unit of the terminal device 2. Specifically, the system control circuitry 24 controls the display circuitry 22, and displays the operation screen and ultrasonic image which are transmitted from the ultrasonic diagnostic apparatus 1. In addition, the system control circuitry 24 receives, via the communication interface circuitry 23, the ultrasonic diagnosis image data and terminal operation screen data from the ultrasonic diagnostic apparatus 1. In the meantime, the received ultrasonic diagnosis image data and terminal operation screen data are only temporarily used, and are not stored in the terminal device 2.

In addition, the system control circuitry 24 accepts an operation instruction from the first operator 3 via the input interface circuitry 21. The system control circuitry 24 generates text information in accordance with an input operation from the second operator 4 who uses the keyboard which the input interface circuitry 21 includes. If the second operator 4 presses a predetermined button on the touch panel which the input interface circuitry 21 includes, the system control circuitry 24 refers to additional information of the image data representing the pressed predetermined button, and generates a command signal corresponding to the additional information. The command signal is a signal which instructs a change of the operation screen, which is displayed on the touch panel that the input interface circuitry 21 of the terminal device 2 includes, to a predetermined operation screen. In addition, the command signal is a signal which instructs the ultrasonic diagnostic apparatus 1 to execute a predetermined function. The command signal includes at least one of information representing an operation screen after a change for changing the operation screen, which is displayed on the touch panel that the input interface circuitry 21 includes, to a predetermined operation screen, and an execution command for instructing the ultrasonic diagnostic apparatus 1 to execute a predetermined function. In addition, the system control circuitry 24 controls the communication interface circuitry 23, and transmits a command signal, which corresponds to the accepted operation instruction, to the ultrasonic diagnostic apparatus 1.

This system control circuitry 24 corresponds to second display control circuitry, marker information generation circuitry, and text information generation circuitry. The second display control circuitry causes the display circuitry 22 to display a compressed image, such that the compressed image is substantially synchronized with the display of the medical image on the monitor 13. The marker information generation circuitry generates marker information including position information indicative of a position on the compressed image, in accordance with an input from the second operator as the user. The marker information may include at least one of size information indicative of the size of the marker, and shape information indicative of the shape of the marker, in addition to the position information. The text generation circuitry generates text information in accordance with an input from the second operator as the user.

Figure 3:
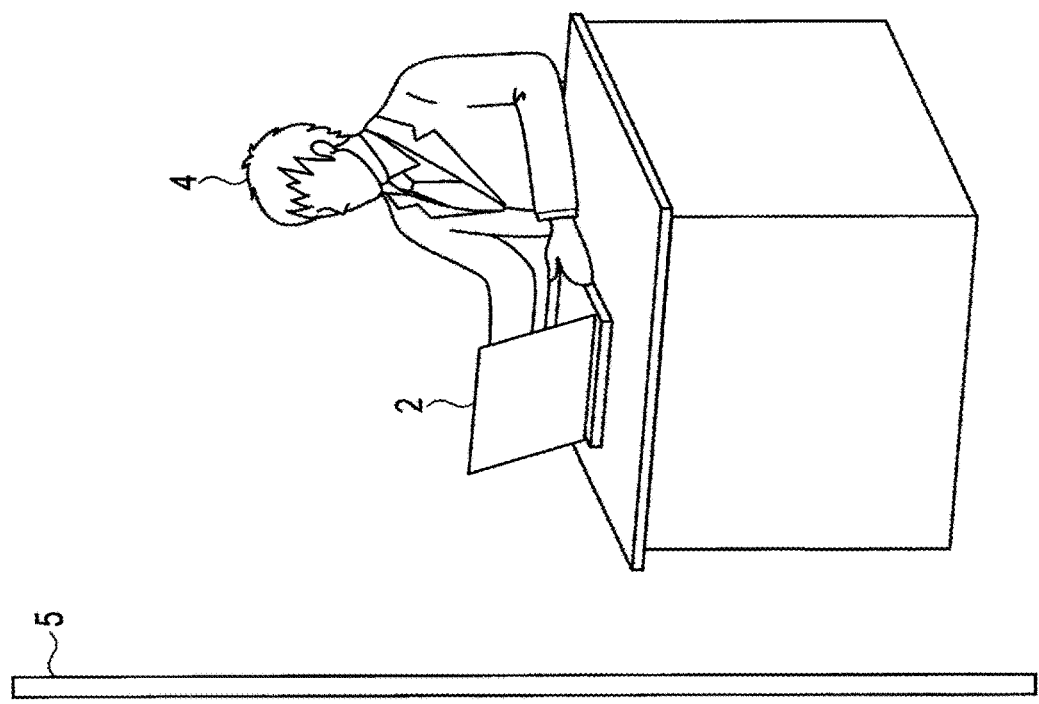
FIG. 3 is a schematic view illustrating an example of a positional relationship between an ultrasonic diagnostic apparatus 1, terminal device 2, a first operator 3, a second operator 4, a curtain 5 and a subject P.
Figure 3:
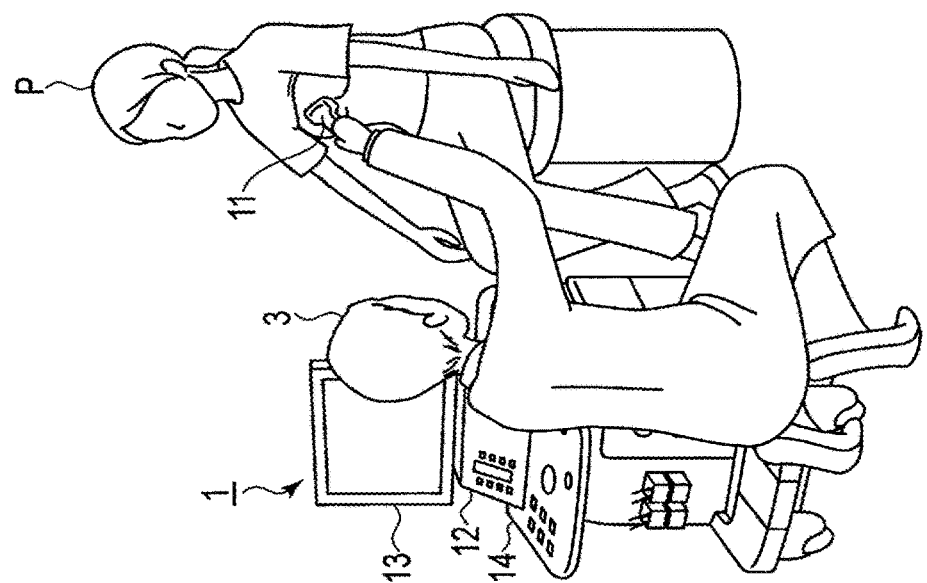

Next, the operation of the first embodiment will be described. FIG. 3 is a schematic view illustrating an example of a positional relationship between the ultrasonic diagnostic apparatus 1, terminal device 2, first operator 3, second operator 4, a curtain 5 and a subject P. As schematically illustrated in FIG. 3, the skilled second operator 4 and the subject P are partitioned by the curtain 5 or the like, and the presence of the second operator 4 and terminal device 2 is not recognized by the subject P. The subject P undergoes an examination of the mammary gland in a sitting position, but, aside from this, for example, there is a case in the subject P undergoes an examination of the abdomen or the like in a decubitus position. In addition, the ultrasonic diagnostic apparatus 1 is disposed in such a direction that the first operator 3 can view the display screen but the subject P cannot view the display screen.

Hereinafter, flows of (1) to (3) will be described, and then the operations for the second operator (supporter) to support the first operator via the terminal device 2 will be described with reference to flows of (4) to (7). Incidentally, it should suffice if any one of the flows (1) to (7) is executed each time an indication is made. The flows of (1) to (7) are as follows: (1) an authentication flow for the terminal device 2 to operate the ultrasonic diagnostic apparatus 1; (2) an ultrasonic image data transfer flow for the ultrasonic diagnostic apparatus 1 to transfer ultrasonic image data to the terminal device 2, based on an operation instruction of the terminal device 2; (3) an operation screen data transfer flow for the ultrasonic diagnostic apparatus 1 to transfer operation screen data to the terminal device 2, based on an operation instruction of the terminal device 2; (4) a flow of sharing an image on which a marker is superimposed; (5) a flow of sharing text information; (6) a flow of sharing a marker and text information; and (7) a flow of sharing an image with a changed image quality.

To begin with, the (1) authentication flow will be described.

(1) Authentication Flow

Figure 4:
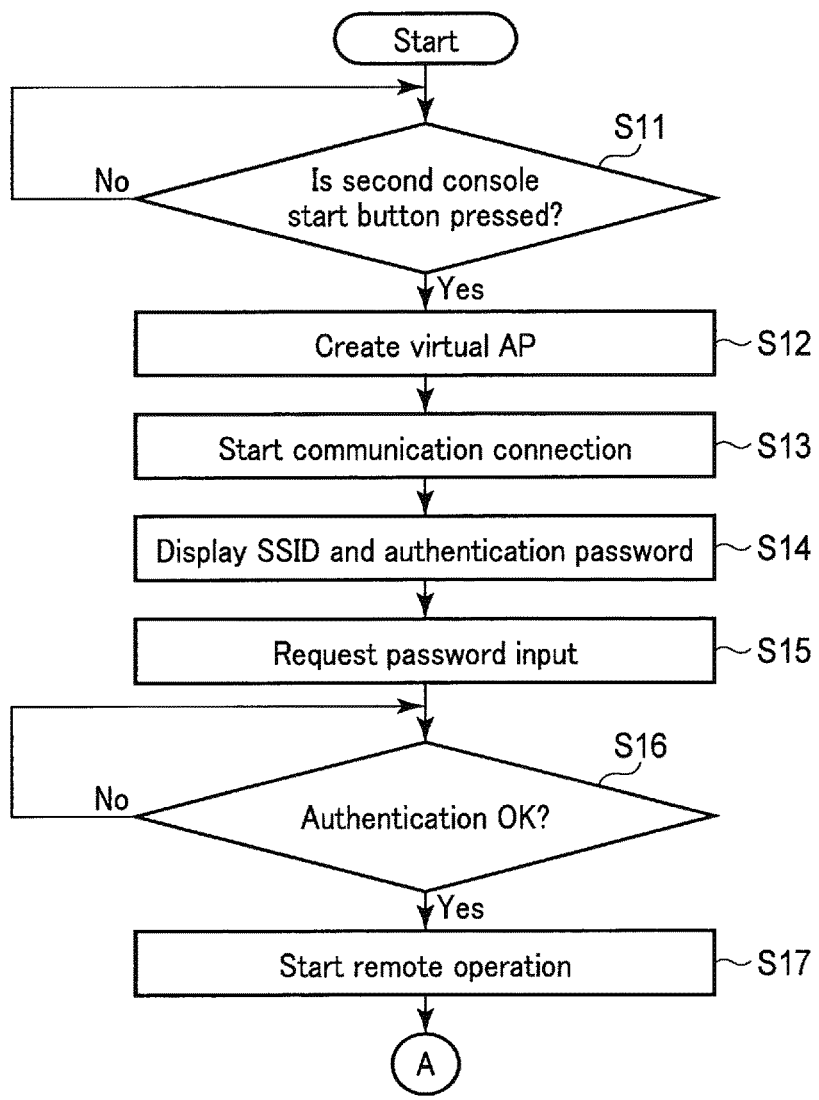
FIG. 4 is an example of a flowchart for describing a flow of an authentication process which various functions of system control circuitry 128 execute.

FIG. 4 is an example of a flowchart for describing the flow of an authentication process which the various functions of the system control circuitry 128 execute.

To start with, the system control circuitry 128 executes the Software AP function 128-3, and stands by until the second console start button is pressed (step S11).

At first, if the second console start button is pressed, the system control circuitry 128 generates a virtual access point (step S12). At this time, the setting of the SSID and password is executed.

After generating the access point in step S12, the system control circuitry 128 establishes a communication connection to the terminal device 2 via the communication interface circuitry 131, based on preset connection information (step S13). Incidentally, the authentication relating to the communication connection between the ultrasonic diagnostic apparatus 1 and terminal device 2 is automatically executed based on preset connection information.

Next, the system control circuitry 128 executes the authentication information display function 128-4, and displays on the monitor 13 the SSID and password which are set in step S12 (step S14). At this time, the system control circuitry 128 may display the SSID and password at a predetermined position on the screen of the monitor 13.

After executing the Software AP function 128-3 and establishing the communication connection to the terminal device 2, the system control circuitry 128 requests the terminal device 2 to execute a password input via the communication interface circuitry 131 (step S15).

The system control circuitry 128 compares the password, which is included in response data to the request for the password input from the terminal device 2, and the password displayed by the authentication information display function 128-4 in step S14. If the password included in the response data and the password displayed by the authentication information display function 128-4 agree (Yes in step S16), the system control circuitry 128 permits the second operator 4 to directly execute a predetermined remote operation relating to the ultrasonic diagnostic apparatus 1 from the terminal device 2 (step S17). In the meantime, if the password included in the response data and the password displayed by the authentication information display function 128-4 do not agree (No in step S16), the system control circuitry 128 generates password input request data once again, and transmits the generated password input request data to the terminal device 2 via the communication interface circuitry 131. If the passwords fail to agree a predetermined number of times, the system control circuitry 128 locks a subsequent process, for example.

(2) Image Data Transfer Flow

The system control circuitry 128 transfers ultrasonic image data from the ultrasonic diagnosis apparatus 1 to the terminal device 2 by controlling the compression ratio. In addition, the system control circuitry 128 transfers ultrasonic image data from the ultrasonic diagnosis apparatus 1 to the terminal device 2 by controlling the compression ratio and terminal display frame rate.

Figure 5:
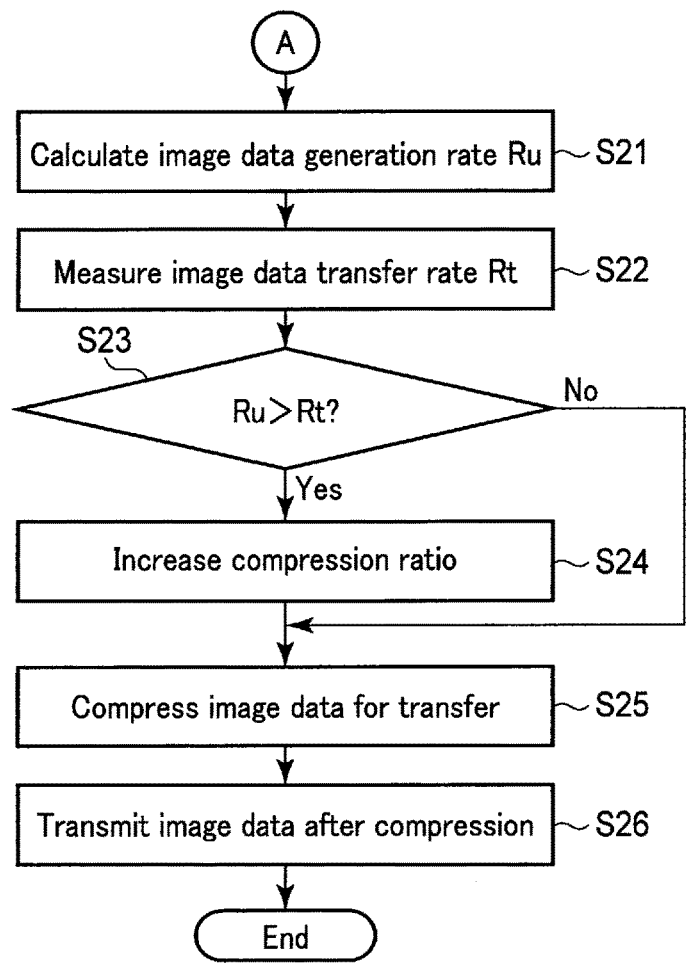
FIG. 5 is a flowchart illustrating an example of a flow of transferring, by controlling a compression ratio, ultrasonic image data from the ultrasonic diagnostic apparatus 1 to the terminal device 2.
Figure 6:
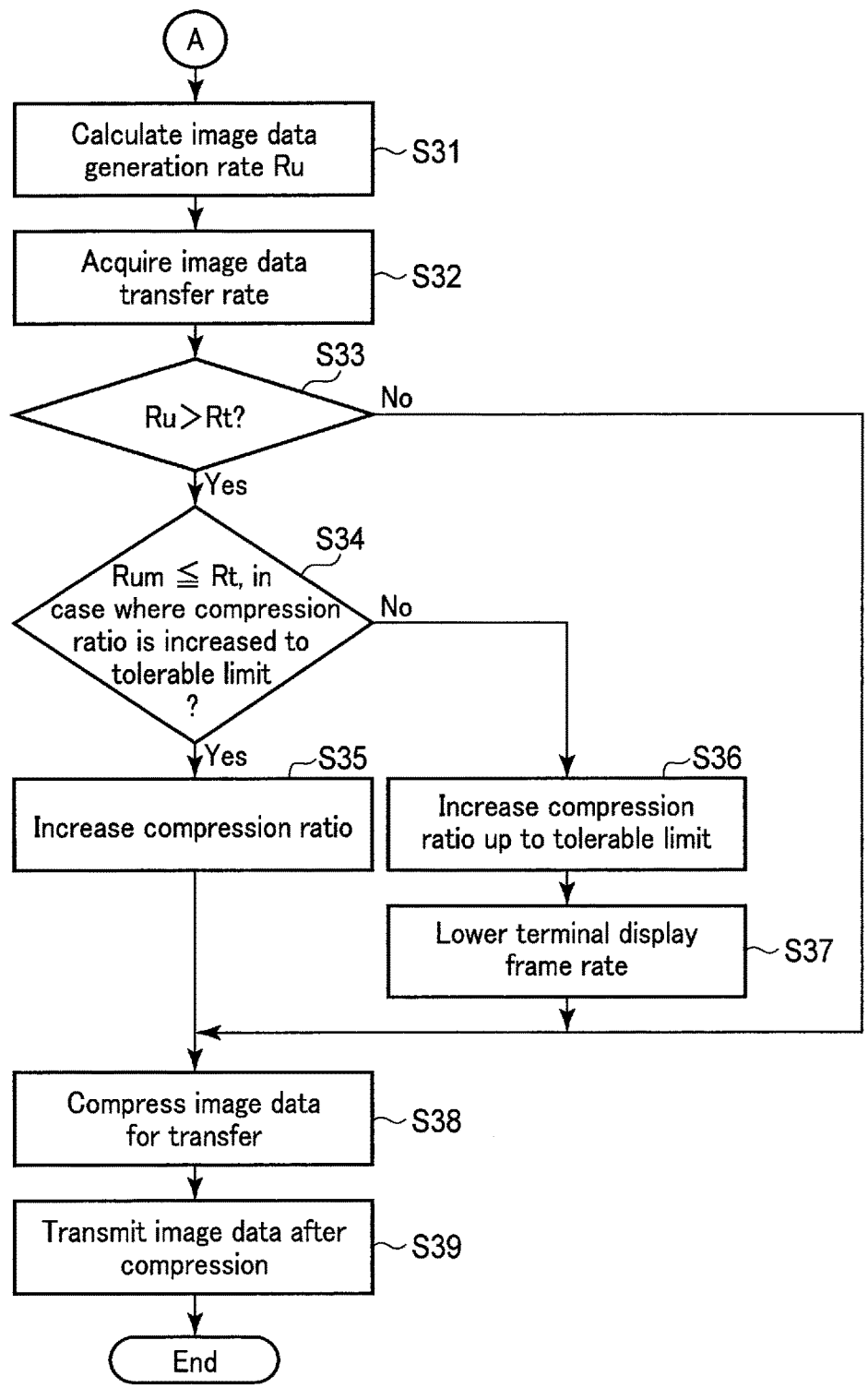
FIG. 6 is a flowchart illustrating an example of a flow of transferring, by controlling a compression ratio and a terminal display frame rate, ultrasonic image data from the ultrasonic diagnostic apparatus 1 to the terminal device 2.
Figure 7:
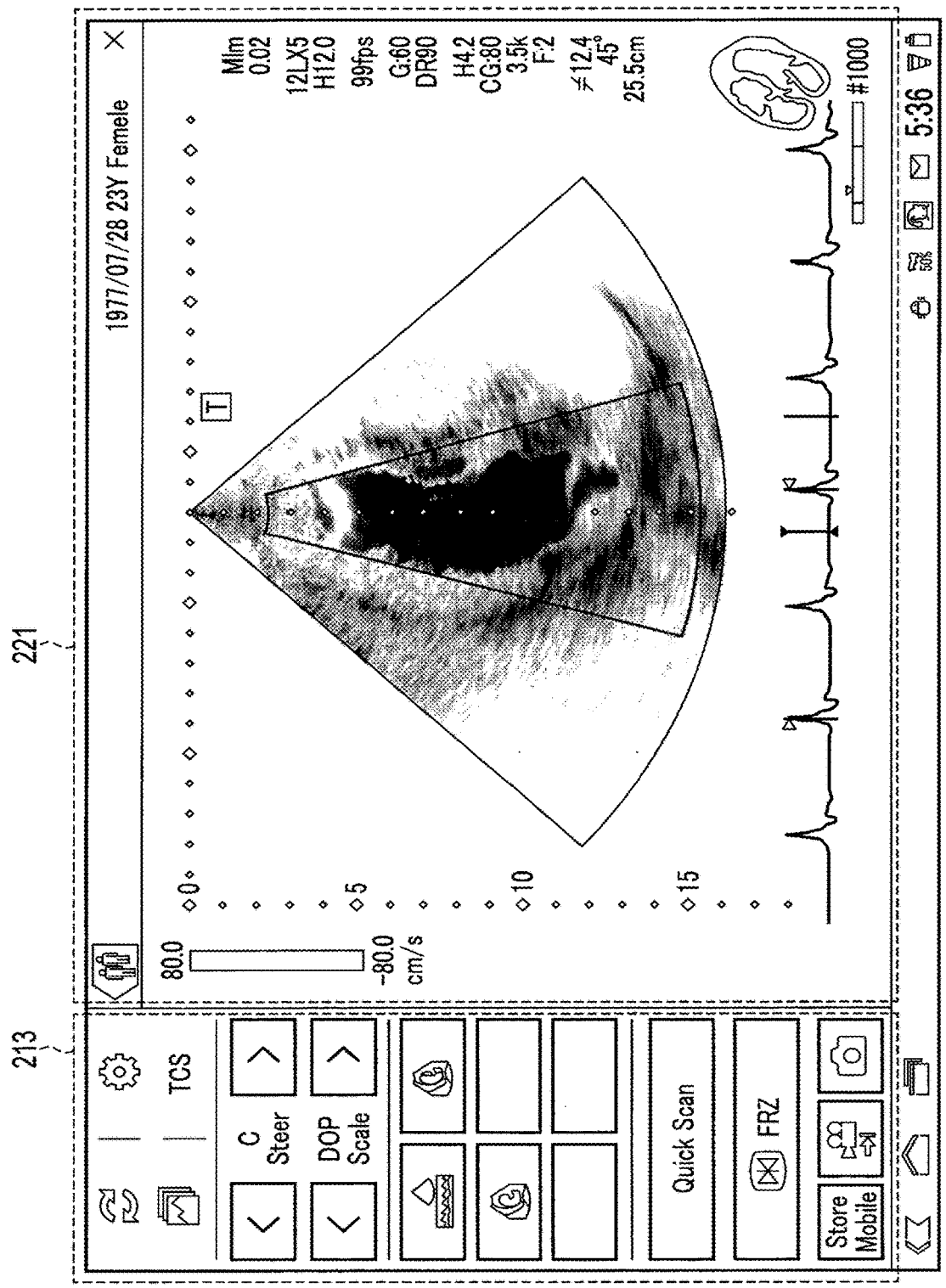
FIG. 7 is a view illustrating examples of an ultrasonic image 221 and an image 213 of a panel switch, which are displayed on display circuitry 22 of the terminal device 2.

FIG. 5 shows an example of a flowchart illustrating an example of a flow of transferring, by controlling the compression ratio, ultrasonic image data from the ultrasonic diagnostic apparatus 1 to the terminal device 2. FIG. 6 shows an example of a flowchart illustrating an example of a flow of transferring, by controlling the compression ratio and terminal display frame rate, ultrasonic image data from the ultrasonic diagnostic apparatus 1 to the terminal device 2. FIG. 7 is a view illustrating examples of an ultrasonic image 221 and an image 213 of a panel switch, which the input interface circuitry 14 of the ultrasonic diagnostic apparatus 1 includes, the ultrasonic image 221 and an image 213 being displayed on the display circuitry 22 of the terminal device 2.

(2-1) Image Data Transfer by Control of Compression Ratio

To start with, the system control circuitry 128 executes the parameter setting function 128-2, and calculates an image data generation rate Ru, based on the data size per 1 frame of the predetermined ultrasonic image generated by the display processing circuitry 126 of the ultrasonic diagnostic apparatus 1, the display frame rate, and the preset compression ratio of ultrasonic image data, which are prestored in the storage circuitry 127 (step S21).

The system control circuitry 128 measures an image data transfer rate Rt of the communication network between the ultrasonic diagnostic apparatus 1 and the terminal device 2 (step S22).

Next, the system control circuitry 128 compares the calculated image data generation rate Ru and the measured image data transfer rate Rt (step S23).

If the result of the comparison shows that Ru is greater than Rt (Yes in step S23), the system control circuitry 128 changes the preset value so that the Ru after compression becomes equal to Rt, that is, so that the preset compression ratio of image data for transfer becomes higher (step S24).

Next, the system control circuitry 128 controls the image encoding circuitry 130, and compresses the ultrasonic image data generated by the display processing circuitry 126, based on the compression ratio that is set in step S24 (step S25). In the meantime, if the result of the comparison shows that Ru is not greater than Rt (No in step S23), the system control circuitry 128 does not change the compression ratio, and compresses the ultrasonic image data generated in the display processing circuitry 126 at the preset compression ratio.

At last, the system control circuitry 128 controls the communication interface circuitry 131, and transmits the compressed ultrasonic image data to the terminal device 2 (step S26).

Incidentally, the item of control in the case of "Yes" in step S23 may be not the compression ratio but the terminal display frame rate.

(2-2) Image Data Transfer by Control of Compression Ratio and Terminal Display Frame Rate When large-capacity DICOM data or the like is transferred between the ultrasonic diagnostic apparatus 1 and the network system such as PACS, the apparatus load of the ultrasonic diagnostic apparatus 1 increases. The increase in apparatus load leads to a factor in a decrease of the effective transfer rate of the communication that is executed between the ultrasonic diagnostic apparatus 1 and terminal device 2. In particular, when wireless communication is executed between the ultrasonic diagnostic apparatus 1 and the network system such as PACS, there may be a case in which the decrease of the effective transfer rate of the communication between the ultrasonic diagnostic apparatus 1 and terminal device 2 becomes conspicuous. In this case, the ultrasonic image data is transferred by controlling, for example, the terminal display frame rate, in addition to the compression ratio.

To start with, the system control circuitry 128 executes the parameter setting function 128-2, and calculates an image data generation rate Ru, based on the data size per 1 frame of the predetermined ultrasonic image generated by the display processing circuitry 126 of the ultrasonic diagnostic apparatus 1, the display frame rate and the preset compression ratio of ultrasonic image data, which are prestored in the storage circuitry 127 (step S31).

The system control circuitry 128 measures an image data transfer rate Rt of the communication network between the ultrasonic diagnostic apparatus 1 and the terminal device 2 (step S32).

The system control circuitry 128 compares the image data generation rate Ru and the image data transfer rate Rt (step S33).

If the result of the comparison shows that Ru is greater than Rt (Yes in step S33), the system control circuitry 128 calculates an image data generation rate Rum in the case of compression at a high compression ratio corresponding to a tolerable limit value, and compares the calculated image data generation rate Rum and the image data transfer rate Rt (step S34).

If the result of the comparison shows that Rum is not greater than Rt (Yes in step S34), the system control circuitry 128 changes the preset value so that the Ru after compression becomes equal to Rt, that is, so that the preset compression ratio of image data for transfer becomes higher (step S35).

If the result of the comparison shows that Rum is greater than Rt (No in step S34), the system control circuitry 128 sets the preset compression ratio of image data for transfer to the tolerable limit value (step S36).

In addition, after step S36, the system control circuitry 128 makes the terminal display frame rate lower than the preset value (step S37).

The system control circuitry 128 controls the image encoding circuitry 130, and compresses the ultrasonic image data generated by the display processing circuitry 126 at the compression ratio that is set in step S35 or step S36 (step S38). In the meantime, if the result of the comparison shows that Ru is not greater than Rt (No in step S33), the system control circuitry 128 does not change the compression ratio, and compresses the ultrasonic image data generated in the display processing circuitry 126 at the preset compression ratio.

At last, the system control circuitry 128 controls the communication interface circuitry 131, and transmits the compressed ultrasonic image data to the terminal device 2 (step S39).

(3) Operation Screen Data Transfer Flow

Figure 8:
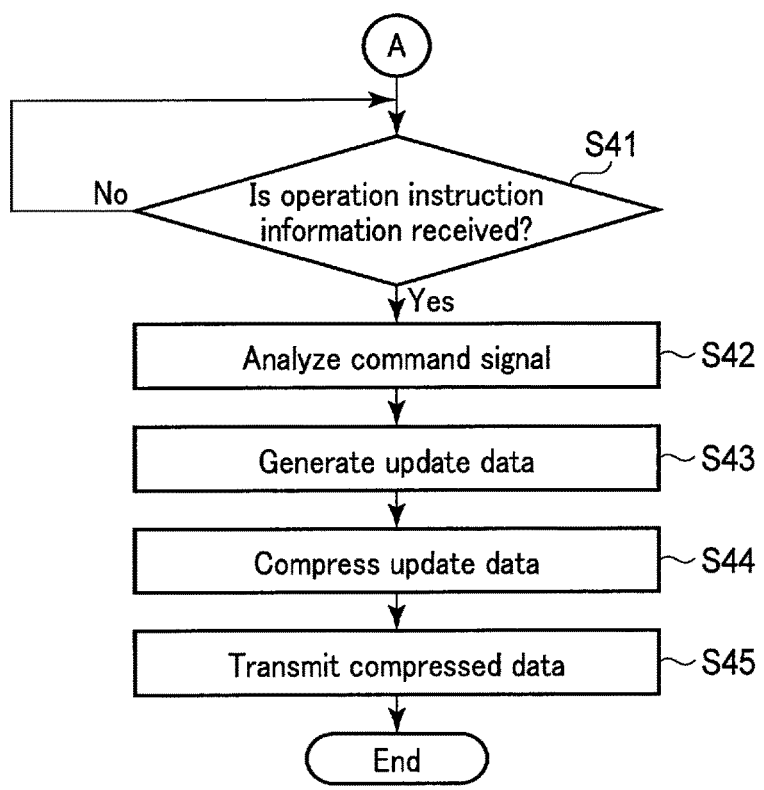
FIG. 8 is a flowchart illustrating an example of a flow of transferring operation screen data from the ultrasonic diagnostic apparatus 1 to the terminal device 2.
Figure 9:
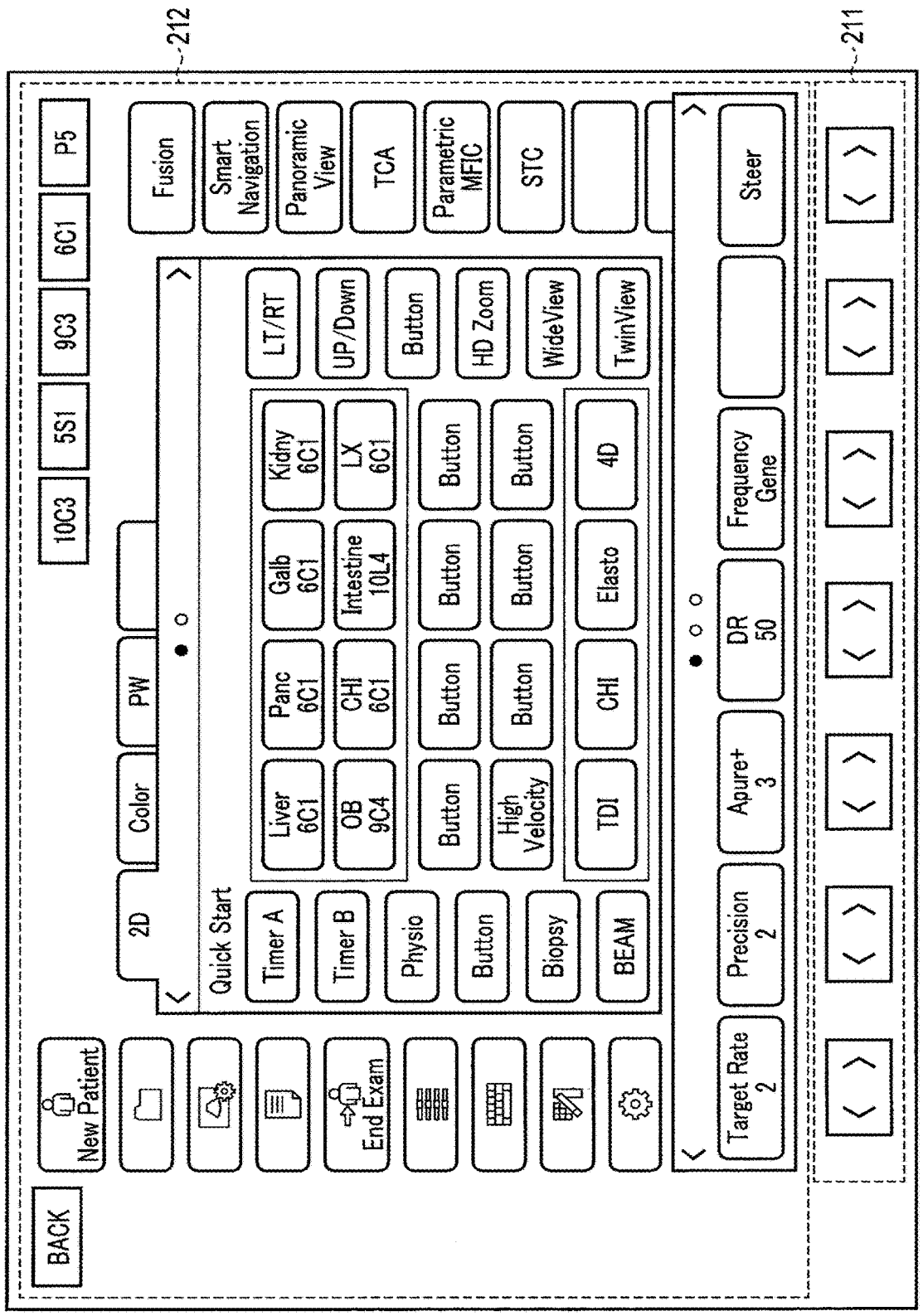
FIG. 9 is a view illustrating an example of an image or the like which is displayed on a touch panel that input interface circuitry 21 of the terminal device 2 includes, the image or the like being displayed on a touch panel that input interface circuitry 14 of the ultrasonic diagnostic apparatus 1 includes.

The system control circuitry 128 transfers terminal operation screen data from the ultrasonic diagnostic apparatus 1 to the terminal device 2. FIG. 8 shows an example of a flowchart illustrating an example of a flow of transferring operation screen data from the ultrasonic diagnostic apparatus 1 to the terminal device 2. FIG. 9 is a view illustrating an example of an image of a touch panel which the input interface circuitry 14 of the ultrasonic diagnostic apparatus 1 includes, the image of the touch panel being displayed on the touch panel that the input interface circuitry 21 of the terminal device 2 includes. In FIG. 9, an image 211 of the panel switch is an example of an image representing the panel switch which the input interface circuitry 14 of the ultrasonic diagnostic apparatus includes. In addition, an image 212 of the touch panel is an example of an image representing the touch panel which the input interface circuitry 14 of the ultrasonic diagnostic apparatus 1 includes. Incidentally, the operation screen data transfer process is started upon the pressing of a TCS (Touch Command Screen) which is included in the image 213 of the panel switch illustrated in FIG.

To start with, the system control circuitry 128 executes the operation screen generation function 128-1, and stands by until a command signal is notified from the terminal device 2 via the communication interface circuitry 131 (step S41).

When the command signal is notified from the terminal device 2, the system control circuitry 128 refers to the notified command signal, and analyzes which image data and which additional information of the image data are necessary as update information, among the plural image data and the additional information of the image data included in the operation screen database prestored in the storage circuitry 127 (step S42).

The system control circuitry 128 acquires, as terminal operation screen data, the image data and additional information of the image data, which are judged to be necessary as update information as a result of the analysis in step S42 (step S43).

The system control circuitry 128 controls the operation screen encoding circuitry 129, and compresses the acquired terminal operation screen data (step S44). Incidentally, the system control circuitry 128 compresses the information amount by taking a difference between terminal operation screen data which neighbor on the time axis.

The system control circuitry 128 controls the communication interface circuitry 131, and transmits the compressed terminal operation screen data to the terminal device 2 (step S45).

(4) Flow of Sharing Image on which Marker is Superimposed

Any one of the flows of (4) to (7) below is executed each time an indication is made, when the second operator (supporter) supports the first operator via the terminal device 2. To begin with, the flow of (4) is described.

Figure 10:
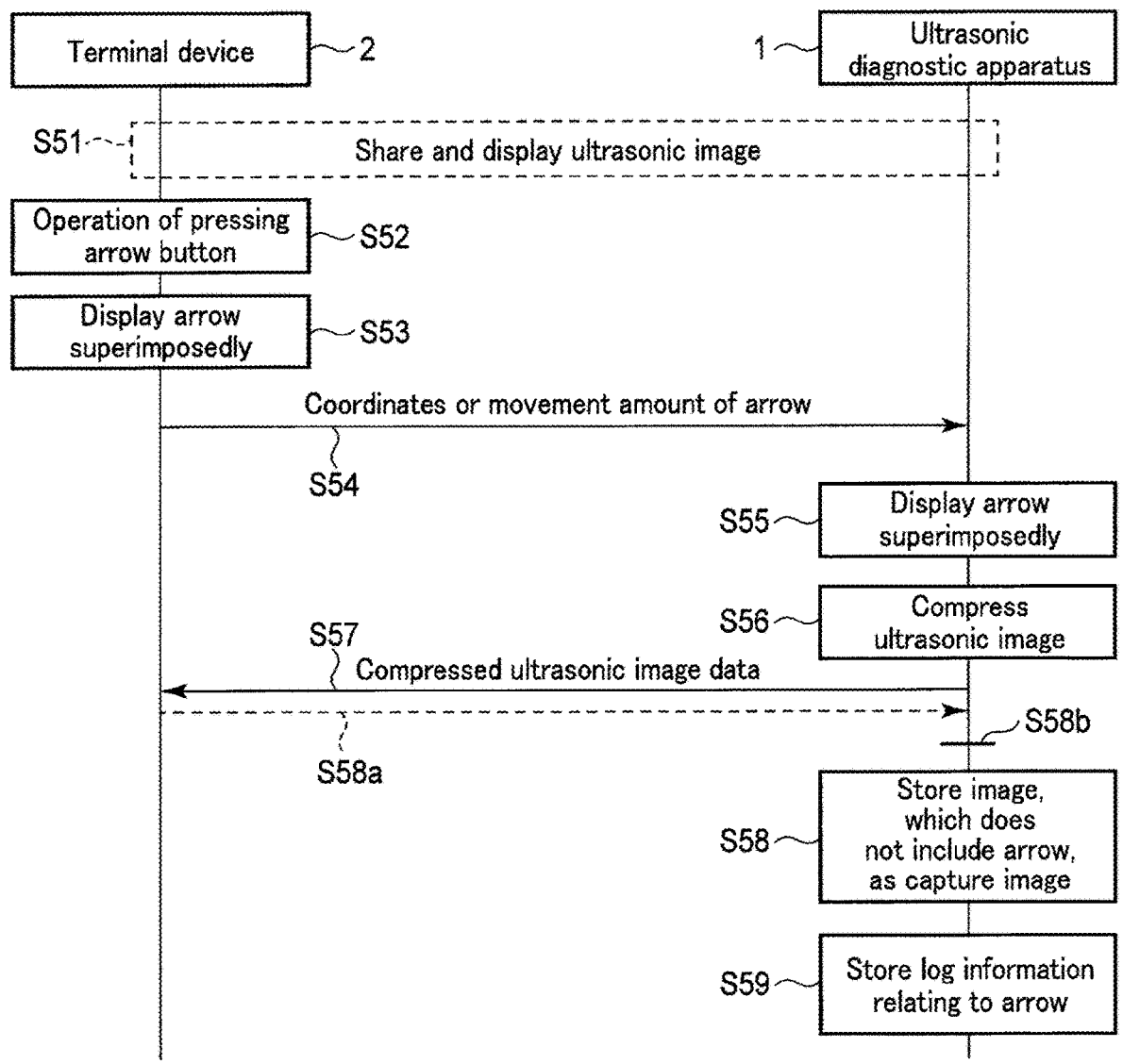
FIG. 10 is a sequence chart for describing an operation of sharing an image on which a marker is superimposed.
Figure 11:
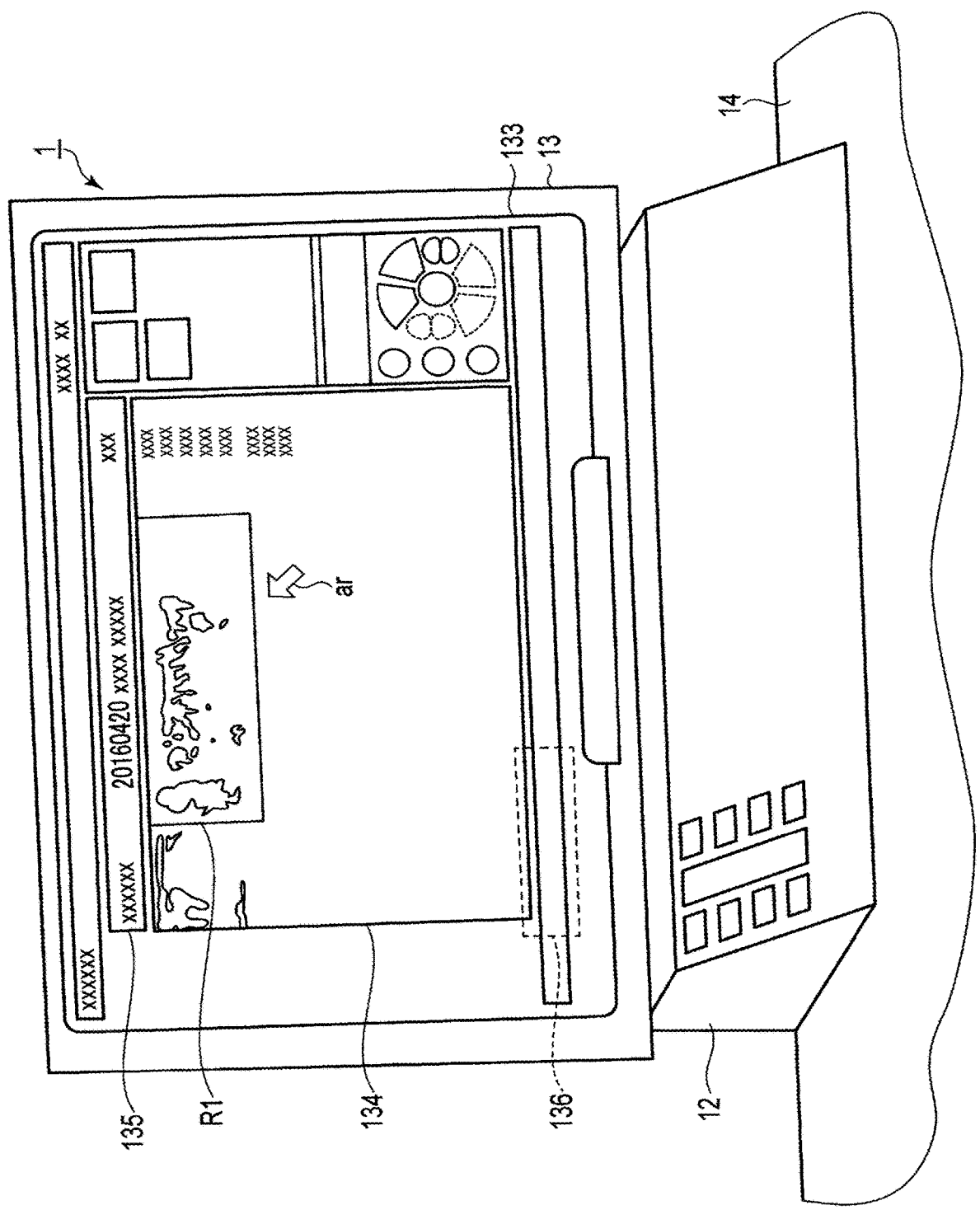
FIG. 11 is a schematic view for describing a screen of the ultrasonic diagnostic apparatus 1 which is used in the operation illustrated in FIG. 10.
Figure 12:
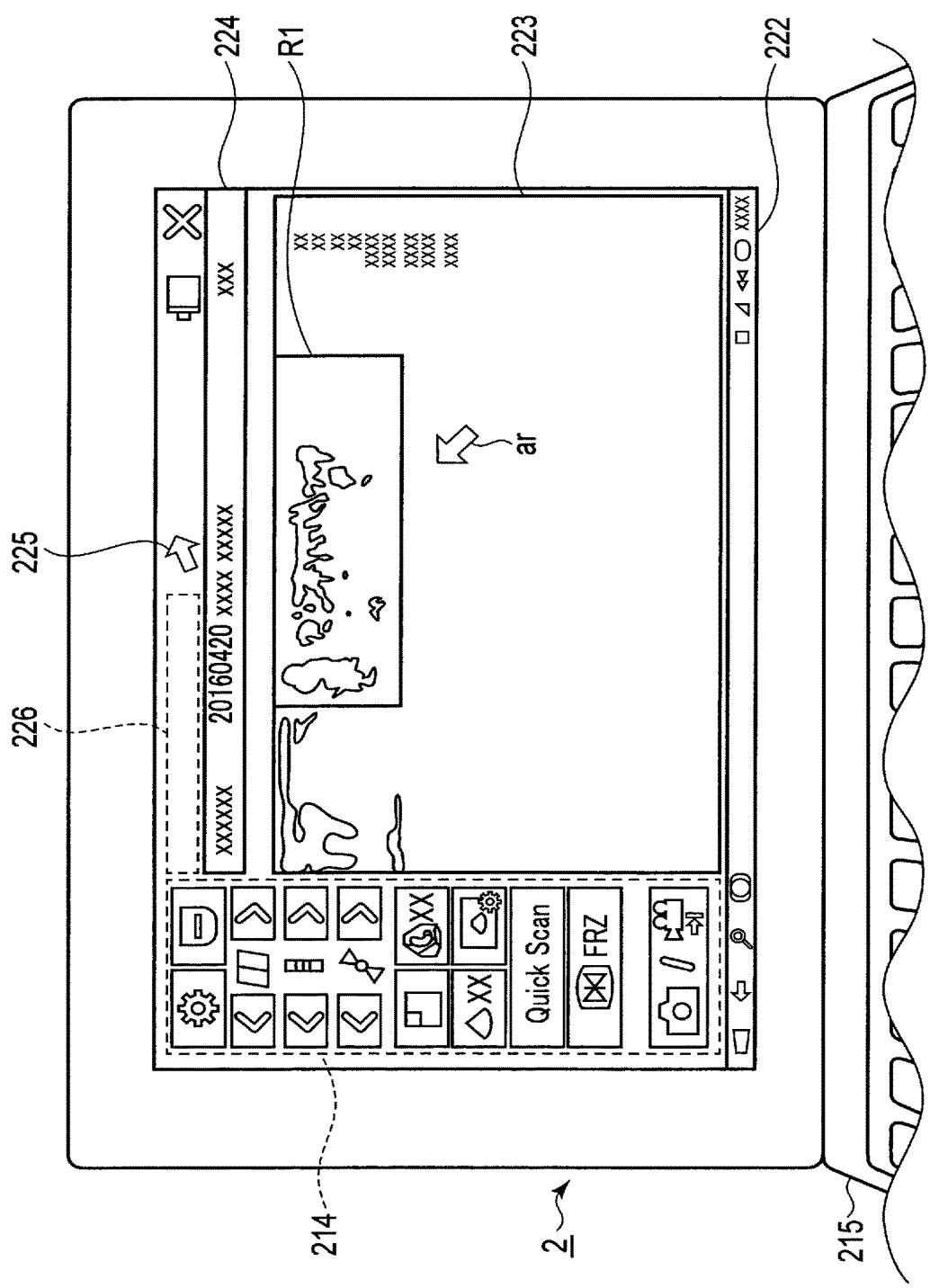
FIG. 12 is a schematic view for describing a screen of the terminal device 2 which is used in the operation illustrated in FIG. 10.
Figure 13:
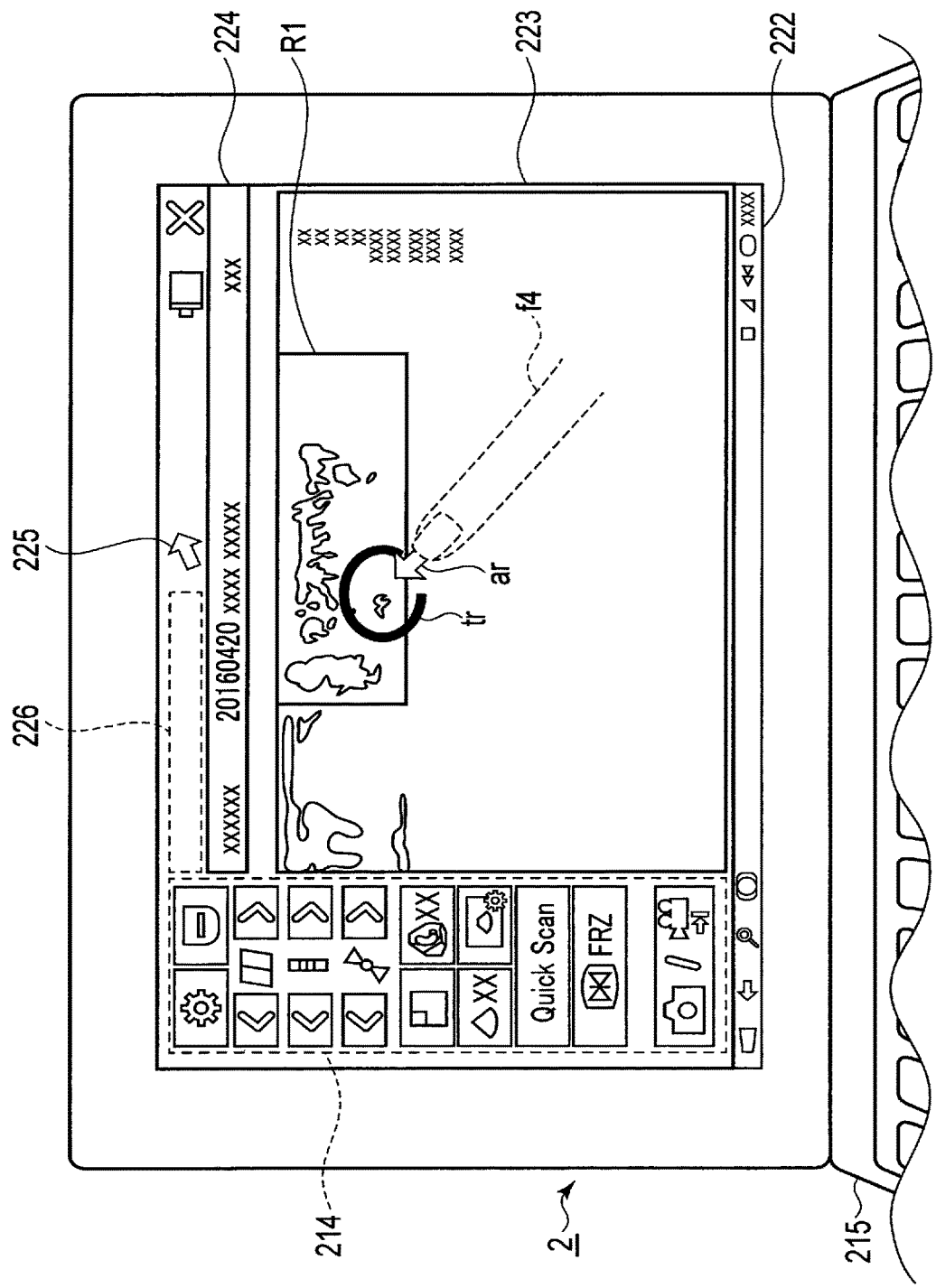
FIG. 13 is a schematic view for describing a screen of the terminal device 2 which is used in a modification of the operation illustrated in FIG. 10.

FIG. 10 is a sequence chart for describing an operation of sharing an image on which a marker is superimposed. FIG. 11, FIG. 12 and FIG. 13 are schematic views for describing screens used in this operation. In the description below, an arrow is used as a marker. Aside from this, an arbitrary image, such as a cross mark or a finger mark, can be used as the marker.

It is now assumed that, as illustrated in FIG. 3, the unskilled first operator 3 operates the ultrasonic diagnostic apparatus 1, and the skilled second operator 4 operates the terminal device 2. Similarly, it is assumed that the skilled second operator 4 and the subject P are partitioned by the curtain or the like, so that the presence of the second operator 4 and terminal device 2 is not recognized by the subject P. In addition, the ultrasonic diagnostic apparatus 1 is disposed in such a direction that the display screen cannot be viewed from the subject P. The situation illustrated in FIG. 3 applies also to the flows of (5) to (7) below.

At this time, the ultrasonic diagnostic apparatus 1 generates, based on the output of the ultrasonic probe 11, ultrasonic image data representing an ultrasonic image, for example, via the ultrasonic transmission/reception circuitry 121, B mode processing circuitry 122, volume data generation circuitry 124 and image processing circuitry 125. In addition, the display processing circuitry 126 causes the monitor 13 to display this ultrasonic image. On the other hand, the image encoding circuitry 130 compresses the ultrasonic image, thereby generating a compressed image. The communication interface circuitry 131 wirelessly transmits the compressed image to the terminal device 2. Specifically, like the above (2) image data transfer flow, the ultrasonic diagnostic apparatus 1 transfers the ultrasonic image data from the ultrasonic diagnostic apparatus 1 to the terminal device 2.

On the other hand, in the terminal device 2, the communication interface circuitry 23 receives the compressed image which is wirelessly transmitted from the ultrasonic diagnostic apparatus 1. The system control circuitry 24 causes the display circuitry 22 to display the compressed image, such that the display of the compressed image is substantially synchronized with the display of the ultrasonic image on the monitor 13.

In this manner, the ultrasonic diagnostic apparatus 1 and terminal device 2 share and display the ultrasonic image which is constantly new on the time axis (step S51).

For example, as illustrated in FIG. 11, it is assumed that the ultrasonic diagnostic apparatus 1 displays, in a screen 133 of the monitor 13, an ultrasonic image 134, additional information 135 of the ultrasonic image 134, and a text display area 136. Here, in the ultrasonic image 134, a region-of-interest R1 may be set, or may not be set. In addition, an arrow ar in the ultrasonic image 134 is not displayed at the time point of this step S51.

On the other hand, as illustrated in FIG. 12, it is assumed that the terminal device 2 displays, in a screen 222, an ultrasonic image 223, additional information 224 of the ultrasonic image 223, an arrow button 225, a text display area 226, and an image 214 of a panel switch for operating the ultrasonic diagnostic apparatus 1. This ultrasonic image 223 is an image which is obtained by compressing the ultrasonic image 134 displayed on the ultrasonic diagnostic apparatus 1. In addition, it is assumed that this terminal device 2 is of the tablet type, and a keyboard 215 is attached to the terminal device 2. An arrow ar in the ultrasonic image 223 is not displayed at the time point of this step S51.

After step S51, the input interface circuitry 21 of the terminal device 2 accepts an operation of the arrow button 225 by the second operator 4 (step S52), and outputs the accepted operation to the system control circuitry 24.

The system control circuitry 24 controls the display circuitry 22 so as to superimpose the arrow ar corresponding to the arrow button 225 on the ultrasonic image 223. Thereby, the display circuitry 22 superimposes and displays the arrow ar on the ultrasonic image 223 (step S53).

Thereafter, the system control circuitry 24 wirelessly transmits the coordinates or movement amount of the arrow ar to the ultrasonic diagnostic apparatus 1 by the communication interface circuitry 23 (step S54). However, the coordinates of the arrow ar immediately after the operation of the arrow button 225 may be set as predetermined coordinates. In addition, in the wireless communication immediately after the operation of the arrow button 225, a command signal for starting the display of the arrow may be transmitted instead of the position information such as the coordinates or movement amount of the arrow ar.

In the meantime, the process of steps S54 to S59 is repeatedly executed. However, in step S54 of the second and following process, the system control circuitry 24 generates, in accordance with the input from the second operator 4, marker information including the position information (the coordinates or movement amount of arrow ar) indicating a position on the ultrasonic image 223 as the compressed image, and wirelessly transmits this marker information to the ultrasonic diagnostic apparatus 1. In addition, for example, if the system control circuitry 24 accepts a slide operation from the second operator 4 for designating the position on the ultrasonic image 223 for the arrow ar, the system control circuitry 24 controls the display circuitry 22 so as to move the arrow ar to the position on the ultrasonic image 223, which is designated by the second operator 4. In this case, the display circuitry 22 moves the arrow ar on the ultrasonic image 223. Thereby, a location of attention on the ultrasonic image 223 is designated by the arrow ar. Alternatively, as illustrated in FIG. 13, the system control circuitry 24 may control the display circuitry 22 so as to display a trace tr of the arrow ar for a predetermined time of about several seconds, in addition to the control to move the arrow ar. This trace tr may be displayed, for example, as a strip having a preset color, or may be displayed as a plurality of arrows ar which are overlapped while being displaced. In these cases, the location of attention on the ultrasonic image 223 is designated as a region surrounded by the trace tr.

After step S54, the system control circuitry 128 of the ultrasonic diagnostic apparatus 1 receives the coordinates or movement amount of the arrow ar via the communication interface circuitry 131. The system control circuitry 128 controls the display processing circuitry 126 so as to superimpose and display the arrow ar on the ultrasonic image 134, based on the coordinates or movement amount of the arrow ar. The display processing circuitry 126 generates ultrasonic image data representing the ultrasonic image 134 on which the arrow ar is superimposed, in order to cause the monitor 13 to display a composite image in which the arrow ar is composited on the ultrasonic image 134. Thereby, the monitor 13 displays the ultrasonic image 134 on which the arrow ar is superimposed, based on the ultrasonic image data generated by the display processing circuitry 126 (step S55). Here, the ultrasonic image 134, on which the arrow ar is superimposed, is the composite image in which the arrow ar is composited on the ultrasonic image 134. Incidentally, the arrow ar displayed in step S55 is displayed by an arrow image which is prepared in advance in the ultrasonic diagnostic apparatus 1, and the arrow ar displayed in step S53 is displayed by an arrow image which is prepared in advance in the terminal device 2. Both arrows ar may have the same size and shape, or may have different sizes and shapes. When the marker information includes size information and shape information, the size and shape of the arrow ar may be determined with reference to the marker information. For example, since the terminal device 2 is small, the arrow ar displayed on the terminal device 2 becomes easier to visually recognize, if the size of the arrow ar on the ultrasonic image, which is displayed on the terminal device 2, is made relatively larger than the size of the arrow ar which is displayed on the ultrasonic diagnostic apparatus 1. In the meantime, when the trace tr of the arrow ar is displayed on the terminal device 2, the display processing circuitry 126 causes the monitor 13 to display the arrow ar and the trace tr thereof on the ultrasonic image 134, based on the coordinates or movement amount of the arrow ar, in accordance with the control of the system control circuitry 128. It should be noted, however, that the trace tr is displayed only for a predetermined time, and is erased after the passing of the predetermined time. For example, the display processing circuitry 126 generates ultrasonic image data representing the ultrasonic image 134 on which the arrow ar and trace tr are superimposed, and generates, after the predetermined time, ultrasonic image data representing the ultrasonic image 134 on which only the arrow ar is superimposed. Incidentally, the ultrasonic image 134, on which the arrow ar and trace tr are superimposed, is a composite image in which the arrow ar and trace tr are composited on the ultrasonic image 134.

After step S55, in accordance with the control of the system control circuitry 128, the image encoding circuitry 130 compresses the ultrasonic image data (ultrasonic image 134 including the arrow ar) generated by the image processing circuitry 125, based on the compression ratio which is set in step S24 (step S56).

After step S56, the system control circuitry 128 controls the communication interface circuitry 131, and transmits the compressed ultrasonic image data to the terminal device 2 (step S57).

In addition, before or after steps S56 and S57, or in parallel with steps S56 and S57, the system control circuitry 128 stores the ultrasonic image 134, which does not include the arrow ar, in the storage circuitry 127 as a capture image, in accordance with a storage request accepted in the terminal device 2 (step S58). For example, if a control signal is wirelessly transmitted from the terminal device 2 in accordance with the storage request (step S58a) and this control signal is received by the communication interface circuitry 131, the system control circuitry 128 may store the capture image in accordance with the received control signal. At this time, the system control circuitry 128 stores the capture image and time information in the storage circuitry 127 by associating the capture image and time information. Incidentally, the capture image can be used, for example, for an explanation to the subject P at a later date. The time information is included, for example, in the additional information 135 of the ultrasonic image 134. In addition, the system control circuitry 128 may store the capture image in accordance with a storage request which is accepted in the input interface circuitry 14. For example, when the input interface circuitry 14 sends a control signal in accordance with the storage request (step S58b), the system control circuitry 128 may store the capture image in accordance with the sent control signal.

In addition, when the composite image, in which the arrow ar is composited on the ultrasonic image 134, is displayed on the monitor 13, the system control circuitry 128 stores log information relating to the arrow ar in the storage circuitry 127, before or after steps S56 to S58, or in parallel with steps S56 to S58 (step S59). The log information includes, for example, the coordinates or movement amount of the arrow ar, and time information. In addition, the log information immediately after the arrow button 225 is pressed may include information indicative of a command signal for starting the display of the arrow, and time information. In the meantime, when the capture image is the ultrasonic image 134, the coordinates received in step S54 may be used as the coordinates of the arrow ar in the log information. Besides, when the capture image is the screen 133 including the ultrasonic image 134, coordinates, which are obtained by correcting the coordinates received in step S54, based on the position of the ultrasonic image 134 in the screen 133, may be used as the coordinates of the arrow ar in the log information. This applies also to the other flows of sharing. The time information is included, for example, in the additional information 135 of the ultrasonic image 134. This log information is usable, for example, such that the arrow ar is superimposed on the capture image, based on the time information. In this case, for example, the system control circuitry 128 specifies the coordinates or movement amount of the arrow ar in the log information, and the capture image in the storage circuitry 127, based on the time information designated by the user. Thereafter, based on the specified result, the system control circuitry 128 causes the monitor 13 to display the arrow ar together with the capture image, by the control of the display processing circuitry 126. Specifically, based on the specified marker information, the system control circuitry 128 displays the composite image in which the marker is composited on the specified medical image.

Thereafter, in accordance with the operation of the arrow ar in the terminal device 2, the process of steps S54 to S59 is repeatedly executed. In step S54 of the second and following process, the system control circuitry 24 generates, in accordance with the input from the second operator 4, marker information including the position information (the coordinates or movement amount of arrow ar) indicating a position on the ultrasonic image 223 as the compressed image, and wirelessly transmits this marker information to the ultrasonic diagnostic apparatus 1. In step S55 of the second and following process, in the same manner as described above, the ultrasonic diagnostic apparatus 1 displays the medical image on which the arrow ar is superimposed, based on the received marker information (the coordinates or movement amount in the received marker information). Steps S56 to S59 are executed in the same manner as described above.

(Modification of the Above (4))

In the above-described (4) flow of sharing an image on which a marker is superimposed, both the terminal device 2 and the ultrasonic diagnostic apparatus 1 execute the process of superimposing the marker. The restriction to this is unnecessary. Such a modification may be made that only the ultrasonic diagnostic apparatus 1 executes the process of superimposing the marker. For example, the configuration of the ultrasonic diagnostic apparatus 1 may be modified such that the ultrasonic diagnostic apparatus 1 generates a new compressed image by compressing the medical image including the marker, and wirelessly transmits this new compressed image to the terminal device 2. Incidentally, the medical image including the marker may be called "composite image". Similarly, the configuration of the terminal device 2 may be modified such that the terminal device 2 receives the new compressed image which is wirelessly transmitted from the ultrasonic diagnostic apparatus 1, and the new compressed image is displayed on the display circuitry 22 such that the newly compressed image is substantially synchronized with the display of the composite image on the monitor 13.

FIG. 14 is a sequence chart for describing a modification of the operation illustrated in FIG. 10. In the operation of this modification, step S53 is omitted and, after step S52, the system control circuitry 24 generates a command signal for starting the display of the arrow ar corresponding to the arrow button 225. Thereafter, the system control circuitry 24 wirelessly transmits, by the communication interface circuitry 23, this command signal to the ultrasonic diagnostic apparatus 1 (step S54*a*). However, in step S54*a*, preset coordinates may be wirelessly transmitted in place of the command signal.

Upon receiving the command signal via the communication interface circuitry 131, the system control circuitry 128 of the ultrasonic diagnostic apparatus 1 controls the display processing circuitry 126 so as to superimpose and display the arrow ar on the ultrasonic image 134. The display processing circuitry 126 generates ultrasonic image data representing the ultrasonic image 134 on which the arrow ar is superimposed. Thereby, in the same manner as described above, the monitor 13 displays the ultrasonic image 134 on which the arrow ar is superimposed (step S55). Specifically, the monitor 13 displays the composite image in which the arrow ar is composited on the ultrasonic image 134.

After step S55, in accordance with the control of the system control circuitry 128, the image encoding circuitry 130 compresses the ultrasonic image data (composite image) generated by the display processing circuitry 126, based on the compression ratio which is set in step S24 (step S56*a*). Subsequently, in the same manner as described above, steps S57 to S57 are executed. Thereafter, in accordance with the operation of the arrow ar in the terminal device 2, the process of steps S54*a* to S59 is repeatedly executed. At this time, the terminal device 2 wirelessly transmits marker information including the coordinates or movement amount of the arrow ar to the ultrasonic diagnostic apparatus 1, in accordance with the operation of the arrow ar. In the same manner as described above, the ultrasonic diagnostic apparatus 1 displays the composite image which is formed of the medical image on which the arrow ar is superimposed, based on the received marker information (the coordinates or movement amount in the received marker information), generates a new compressed image by compressing the composite image, and wirelessly transmits the new compressed image to the terminal device 2. The terminal device 2 receives the new compressed image which is wirelessly transmitted from the ultrasonic diagnostic apparatus 1, and causes the display circuitry 22 to display the new compressed image such that the new compressed image is substantially synchronized with the display of the composite image on the monitor 13. Similarly, in the same manner as described above, the ultrasonic diagnostic apparatus 1 stores the capture image and log information. However, in steps S54*a* to S59 which are repeatedly executed, the coordinates or movement amount of the arrow ar is used in place of the command signal for starting the display of the arrow.

(5) Flow of Sharing Text Information

The flow of (5) is a modification of the flow of (4). For example, an item, which is difficult to communicate by the marker, can be transmitted as text information.

Figure 15:
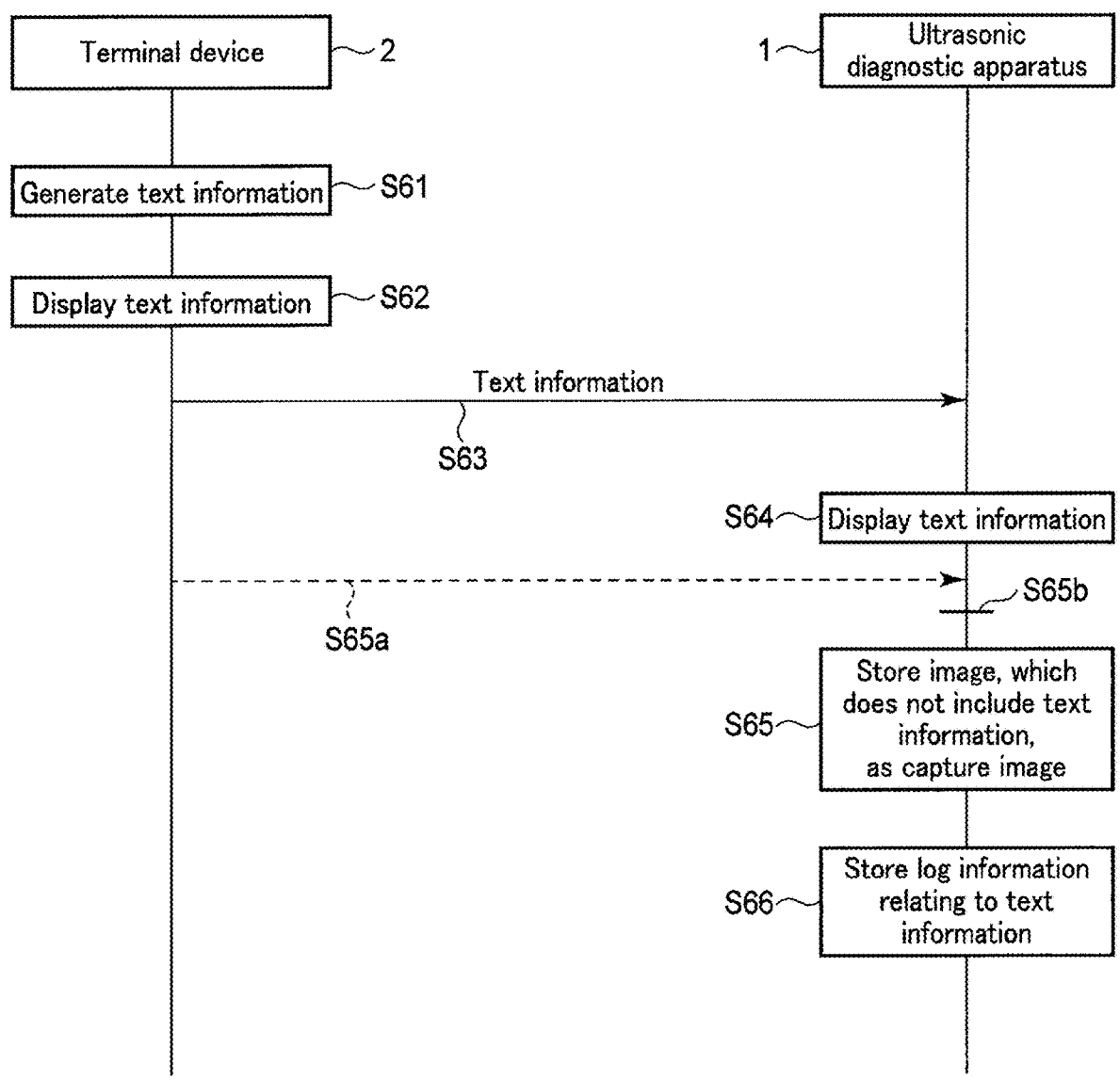
FIG. 15 is a sequence chart for describing an operation of sharing text information.

FIG. 15 is a sequence chart for describing an operation of sharing text information.

Like the above, it is now assumed that, in the situation illustrated in FIG. 3, as described in step S51, the ultrasonic diagnostic apparatus 1 and terminal device 2 share and display the ultrasonic image, and the arrow ar is not displayed in the screens of FIG. 11 and FIG. 12.

At this time, the input interface circuitry 21 of the terminal device 2 converts an operation of the keyboard 215 by the second operator 4 to an electric signal, and inputs the electric signal to the system control circuitry 24.

The system control circuitry 24 generates text information in accordance with the input electric signal (step S61), and controls the display circuitry 22 so as to display the text information on the text display area 226. Thereby, the display circuitry 22 displays the text information on the text display area 226 which is located at a different position from the ultrasonic image 223 (step S62). Incidentally, the text information constitutes a sentence of an arbitrary number of characters or less, which is contained within the text display area 226. In addition, the text information may be generated from electric signals indicative of individual characters, or may be generated from an electric signal designating a fixed-form sentence.

After step S62, upon accepting an operation of a transmission button (not shown) by the second operator 4, the system control circuitry 24 wirelessly transmits, by the communication interface circuitry 23, the text information, which is being displayed on the text display area 226, to the ultrasonic diagnostic apparatus 1 (step S63). In the meantime, when text information is Japanese which involves kana-kanji conversion (an operation of "Enter" key), the operation of the transmission button is executed as described above. However, when text information is a language, such as English, which does not involve kana-kanji conversion, such a modification is possible that the transmission button is omitted and text information is transmitted by the operation of the "Enter" key. In any case, the system control circuitry 24 transmits text information at a punctuation of a sentence, by the operation of the second operator.

Upon receiving the text information via the communication interface circuitry 131, the system control circuitry 128 of the ultrasonic diagnostic apparatus 1 controls the display processing circuitry 126 so as to cause the monitor 13 to display the text information together with the ultrasonic image 134. At this time, the display processing circuitry 126 generates screen data representing the screen 133 which includes the text display area 136 in which the text information is described, and the ultrasonic image 134. By displaying this screen 133, the monitor 13 displays the text information together with the ultrasonic image 134 (step S64).

When both the text information and the ultrasonic image 134 are displayed, the system control circuitry 128 generates, as a capture image, image data of the screen 133 including the text display area 136, which does not include the text information, and the ultrasonic image 134. In addition, when both the text information and the ultrasonic image 134 are displayed, the system control circuitry 128 stores this capture image in the storage circuitry 127 in accordance with a storage request accepted in the terminal device 2 (step S65). For example, if a control signal is wirelessly transmitted in accordance with the storage request from the terminal device 2 (step S65a) and this control signal is received by the communication interface circuitry 131, the system control circuitry 128 may store the capture image in the storage circuitry 127 in accordance with the received control signal. At this time, the system control circuitry 128 stores the capture image and time information in the storage circuitry 127 by associating the capture image and time information. The time information is included, for example, in the additional information 135 of the ultrasonic image 134. In addition, the system control circuitry 128 may store the capture image in accordance with a storage request which is accepted in the input interface circuitry 14. For example, when the input interface circuitry 14 sends a control signal in accordance with the storage request (step S65b), the system control circuitry 128 may store the capture image in the storage circuitry 127 in accordance with the sent control signal.

After step S65, the system control circuitry 128 stores log information relating to the text information in the storage circuitry 127 (step S66). The log information includes, for example, the text information and time information. The time information is included, for example, in the additional information 135 of the ultrasonic image 134. This log information is usable, for example, such that the text information is superimposed on the text display area 136 in the capture image, based on the time information. In this case, for example, the system control circuitry 128 specifies the text information in the log information, and the capture image in the storage circuitry 127, based on the time information designated by the user. Thereafter, the system control circuitry 128 causes the monitor 13 to display the text information together with the capture image, by the control of the display processing circuitry 126.

(6) Flow of Sharing of Marker and Text Information

The flow of (6) is an example of a combination of the above-described flows of (4) and (5).

FIG. 16 is a sequence chart for describing an operation of sharing a marker and text information.

Like the above, it is now assumed that, in the situation illustrated in FIG. 3, as described in step S51, the ultrasonic diagnostic apparatus 1 and terminal device 2 share and display the ultrasonic image, and the arrow ar is not displayed in the screens of FIG. 11 and FIG. 12.

At this time, like steps S52 and S53, the terminal device 2 superimposes and displays the arrow ar corresponding to the arrow button 225 on the ultrasonic image 223, by the operation of the arrow button 225 by the second operator 4 (step S71).

In addition, like steps S61 and S62, the terminal device 2 generates text information in accordance with the operation of the keyboard 215 by the second operator 4, and displays the text information on the text display area 226 (step S72).

After step S72, upon accepting the operation of the transmission button (not shown) by the second operator 4, the system control circuitry 24 wirelessly transmits, by the communication interface circuitry 23, the text information, which is being displayed, and the coordinates or movement amount of the arrow ar to the ultrasonic diagnostic apparatus 1 (step S73). Incidentally, step S73 is not limited to this example, and step S73 may be executed in two steps, namely, the step of transmitting the text information and the step of transmitting the coordinates or movement amount of the arrow ar.

Upon receiving the text information and the coordinates or movement amount of the arrow ar via the communication interface circuitry 131, the system control circuitry 128 of the ultrasonic diagnostic apparatus 1 displays, by the display processing circuitry 126 and monitor 13, the text information on the text display area 136, in the same manner as described above (step S74).

In parallel with step S74, the system control circuitry 128 displays the ultrasonic image 134 on which the arrow ar is superimposed, based on the coordinates or movement amount of the arrow ar, in the same manner as described above (step S75). Incidentally, like the above, the system control circuitry 128 may also display the trace tr of the arrow ar.

After step S75, like step S56, in accordance with the control from the system control circuitry 128, the image encoding circuitry 130 compresses the ultrasonic image data which does not include the arrow ar (step S76). In addition, the system control circuitry 128 controls the communication interface circuitry 131, and transmits the compressed ultrasonic image data to the terminal device 2 (step S77).

In addition, before or after steps S76 and S77, or in parallel with steps S76 and S77, the system control circuitry 128 stores the image data of the screen 133, which includes the text display area 136 that does not include the text information, and the ultrasonic image 134 that does not include the arrow ar, in the storage circuitry 127 as a capture image, in accordance with a storage request accepted in the terminal device 2 (step S78). For example, if a control signal is wirelessly transmitted from the terminal device 2 in accordance with the storage request (step S78a) and this control signal is received by the communication interface circuitry 131, the system control circuitry 128 may store the capture image in accordance with the received control signal. At this time, the system control circuitry 128 stores the capture image and time information in the storage circuitry 127 by associating the capture image and time information. The time information is included, for example, in the additional information 135 of the ultrasonic image 134. In addition, the system control circuitry 128 may store the capture image in accordance with a storage request which is accepted in the input interface circuitry 14. For example, when the input interface circuitry 14 sends a control signal in accordance with the storage request (step S78b), the system control circuitry 128 may store the capture image in accordance with the sent control signal.

In addition, before or after step S78, or in parallel with step S78, the system control circuitry 128 stores log information relating to the text information and the arrow ar in the storage circuitry 127 (step S79). The log information includes, for example, the text information, the coordinates or movement amount of the arrow ar, and time information. The time information is included, for example, in the additional information 135 of the ultrasonic image 134. This log information is usable, for example, such that the text information is superimposed on the text display area 136 in the capture image and the arrow ar is superimposed on the ultrasonic image 134 in the capture image, based on the time information. In this case, for example, the system control circuitry 128 specifies the coordinates or movement amount of the arrow ar in the log information, the text information in the log information, and the capture image in the storage circuitry 127, based on the time information designated by the user. Thereafter, based on the specified result, the system control circuitry 128 causes the monitor 13 to display the text information and the arrow ar together with the capture image, by the control of the display processing circuitry 126.

In the meantime, as regards the arrow ar functioning as the marker, the above flow of (6) can be implemented by being modified like the modification illustrated in FIG. 14. Specifically, like the modification illustrated in FIG. 14, the above flow of (6) can be implemented by being modified such that the arrow ar is superimposed by only the ultrasonic diagnostic apparatus 1 between the terminal device 2 and ultrasonic diagnostic apparatus 1.

(7) Flow of Sharing Image with Changed Image Quality

The flow of (7) is a modification of the above-described (5). In the flow (7), for example, when the second operator 4 judges that the image should be made easier to view, the second operator 4 executes an operation of changing an image quality parameter, after giving an advance notice, by text information, to the effect that the image quality parameter is to be changed.

FIG. 17 is a sequence chart for describing an operation of sharing an image with a changed image quality.

Like the above, it is now assumed that, in the situation illustrated in FIG. 3, as described in step S51, the ultrasonic diagnostic apparatus 1 and terminal device 2 share and display the ultrasonic image, and the arrow ar is not displayed in the screens of FIG. 11 and FIG. 12.

Subsequently, like steps S61 to S66, it is assumed that the ultrasonic diagnostic apparatus 1 and terminal device 2 share and display the text information which is generated in accordance with the operation of the terminal device 2 (steps S81 to S86). However, it is assumed that the text information in this example has content which gives an advance notice of a change to the image quality parameter of the ultrasonic image 223, such as "the image quality parameter xx is changed from now." Incidentally, the term "change" may be read as "increase", "decrease" or "adjustment".

After step S86, the input interface circuitry 21 of the terminal device 2 inputs an electric signal indicating the coordinates of an operation position to the system control circuitry 24, in accordance with the operation, by the second operator 4, of the image 214 of the panel switch for operating the ultrasonic diagnostic apparatus 1.

Based on the coordinates indicated by the input electric signal, the system control circuitry 24 refers to the additional information of this image 214, and generates a command signal for changing the image quality parameter in accordance with the additional information (step S87). Thereafter, the system control circuitry 24 transmits the command signal to the ultrasonic diagnostic apparatus 1 by the communication interface circuitry 23 (step S88).

The system control circuitry 128 of the ultrasonic diagnostic apparatus 1 receives the command signal via the communication interface circuitry 131. Based on the command signal, the system control circuitry 128 controls the display processing circuitry 126 so as to change the image quality parameter. The display processing circuitry 126 generates ultrasonic image data representing the ultrasonic image 134 with the image quality parameter that has been changed. Thereby, the monitor 13 displays the ultrasonic image 134 with the changed image quality parameter, based on the ultrasonic image data generated by the display processing circuitry 126 (step S89).

After step S89, in accordance with the control from the system control circuitry 128, the image encoding circuitry 130 compresses the ultrasonic image data (ultrasonic image 134 with the changed image quality) generated by the display processing circuitry 126, based on the compression ratio which is set in step S24 (step S90).

After step S90, the system control circuitry 128 controls the communication interface circuitry 131, and transmits the compressed ultrasonic image data to the terminal device 2 (step S91). Based on this ultrasonic image data, the terminal device 2 displays the ultrasonic image 223 with the changed image quality.

In addition, before or after step S91, or in parallel with step S91, the system control circuitry 128 of the ultrasonic diagnostic apparatus 1 stores the image data of the screen 133, which includes the text display area 136 that does not include the text information, and the ultrasonic image 134 with the changed image quality, in the storage circuitry 127 as a capture image (step S92). At this time, the system control circuitry 128 stores the capture image and time information in the storage circuitry 127 by associating the capture image and time information. The time information is included, for example, in the additional information 135 of the ultrasonic image 134.

In addition, before or after steps S89 to S92, or in parallel with steps S89 to S92, the system control circuitry 128 stores log information relating to the command signal of step S88 in the storage circuitry 127 (step S93). The log information includes, for example, information indicative of the command signal, and time information. The time information is included, for example, in the additional information 135 of the ultrasonic image 134. This log information is usable, for example, such that the information indicative of the command signal is superimposed on an area different from the ultrasonic image 134 in the capture image, based on the time information. In this case, for example, the system control circuitry 128 specifies the information indicative of the command signal in the log information, and the capture image in the storage circuitry 127, based on the time information designated by the user. Thereafter, the system control circuitry 128 causes the monitor 13 to display the information indicative of the command signal together with the capture image, by the control of the display processing circuitry 126.

As has been described above, according to the first embodiment, the following advantageous effects can be obtained.

As regards the above (1) authentication flow, the system control circuitry 128 executes the authentication information display function 128-4, and displays, for example, the preset SSID and password on the monitor 13. Specifically, only the first operator 3, who can directly view the ultrasonic diagnostic apparatus 1, is allowed to have the access right. Thereby, it is possible to reduce the risk of a communication connection and remote operation by a third party without the right.

In addition, as regards the above (1) authentication flow, the password, which the authentication function 128-5 of the system control circuitry 128 uses at the time of authentication, is the one-time password which is updated at each time of a communication connection request, or is updated periodically. Thereby, it is possible to reduce the risk of a communication connection and remote operation by a third party without the right. In the implementation of this, for example, when the password displayed at a predetermined position on the screen of the monitor 13 has been input to the terminal device 2, the communication between the ultrasonic diagnostic apparatus 1 and terminal device 2 may be permitted. In this case, the one-time password can easily be input, and the input one-time password can easily be authenticated.

As regards the above (2) ultrasonic image data transfer flow, the system control circuitry 128 calculates the image data generation rate Ru. The system control circuitry 128 measures the image data transfer rate Rt of the communication network between the ultrasonic diagnostic apparatus 1 and the terminal device 2. The system control circuitry 128 compares the calculated image data generation rate Ru and the measured image data transfer rate Rt. If the comparison result shows that the Ru is greater than Rt, the system control circuitry 128 changes the preset value, for example, so that the Ru after compression becomes equal to Rt, that is, so that the preset compression ratio of the image data for transfer becomes higher. The system control circuitry 128 compresses the ultrasonic image data which is generated by the display processing circuitry 126, and transmits the compressed ultrasonic image data to the terminal device 2.

Specifically, by lowering the image quality of the ultrasonic image which is represented by the ultrasonic image data generated by the display processing circuitry 126, the system control circuitry 128 transmits the ultrasonic image data without lowering the frame rate of the ultrasonic image that is transmitted to the terminal device 2. Thereby, the second operator 4 can confirm the ultrasonic image in real time on the terminal device 2, even when the acoustic frame rate of the ultrasonic diagnostic apparatus 1 is high and the calculated image data generation rate Ru is higher than the measured image data transfer rate Rt.

As regards the above (3) operation screen data transfer flow, the ultrasonic diagnostic apparatus 1 and terminal device 2 are wirelessly communicably connected. In addition, the system control circuitry 128 acquires the terminal operation screen data, compresses the acquired terminal operation screen data, and wirelessly transmits the compressed terminal operation screen data to the terminal device 2. Thereby, the second operator 4 can display, on the touch panel that the input interface circuitry 21 of the terminal device 2 includes, the image representing the operation screen including the image of the panel switch and the image of the touch panel, which the input interface circuitry 14 of the ultrasonic diagnostic apparatus 1 includes. Accordingly, even when it is difficult for the second operator 4 to directly operate the console of the ultrasonic diagnostic apparatus 1, the second operator 4 can perform the operation for image diagnosis. This applies also to, for example, cases other than the present embodiment (a case in which the first operator 3 and second operator 4 are the same person).

Additionally, as regards the above (3) operation screen data transfer flow, the system control circuitry 128 transmits the terminal operation screen data to the terminal device 2 each time the system control circuitry 128 acquires the terminal operation screen data. Thereby, a new operation screen can be displayed, as needed, on the touch panel which the input interface circuitry 21 of the terminal device 2 includes.

Besides, as regards the above (3) operation screen data transfer flow, the system control circuitry 128 controls the operation screen encoding circuitry 129, and compresses the acquired terminal operation screen data. At this time, the information amount is compressed by taking a difference between terminal operation screen data which neighbor on the time axis. Thereby, the communication data amount between the ultrasonic diagnostic apparatus 1 and terminal device 2 can be reduced.

In addition, as regards the above (3) operation screen data transfer flow, the system control circuitry 128 controls the communication interface circuitry 131, and starts the transmission of the terminal operation screen data by using as a trigger the reception of the command signal from the terminal device 2. Thereby, the operation screen corresponding to the request of the second operator 4 can be displayed on the touch panel which the input interface circuitry 21 of the terminal device 2 includes.

As regards the above (4) flow of sharing the image on which the marker is superimposed, the ultrasonic diagnostic apparatus 1 functioning as the medical diagnostic apparatus generates a medical image based on the output from the ultrasonic probe 11, and causes the monitor 13, which functions as the first display circuitry, to display the medical image. In addition, the ultrasonic diagnostic apparatus 1 compresses the medical image, and wirelessly transmits this first compressed image to the terminal device 2.

The terminal device 2 receives the first compressed image which is wirelessly transmitted, and causes the display circuitry 22, which functions as the second display circuitry, to display the first compressed image such that the display of the first compressed image is substantially synchronized with the display of the medical image on the monitor 13. In addition, in accordance with the input from the user, the terminal device 2 generates the marker information including the position information indicative of the position on the first compressed image.

The ultrasonic diagnostic apparatus 1 receives the marker information which is wirelessly transmitted from the terminal device 2, and causes the monitor 13 to display the composite image in which the marker is composited on the medical image, based on the marker information.

In this manner, while the ultrasonic diagnostic apparatus 1 and terminal device 2 are displaying the common medical image and compressed image thereof, the marker, which is designated by the terminal device 2, is displayed on each of the terminal device 2 and ultrasonic diagnostic apparatus 1. Accordingly, based on the marker displayed on the ultrasonic diagnostic apparatus 1, even the unskilled first operator 3 can execute a proper operation, without causing anxiety to the subject P.

Besides, when the ultrasonic diagnostic apparatus 1 displays, based on the marker information, the trace of the marker in the composite image for a predetermined time, an improvement in visibility of the first operator 3 and an improvement in operability of the second operator 4 can be expected.

In addition, as regards the above (4) flow of sharing the image on which the marker is superimposed, when the composite image is being displayed, the ultrasonic diagnostic apparatus 1 stores the medical image, which constitutes the composite image, and the time information in the storage circuitry 127 by associating the medical image and the time information. In addition, when the composite image is being displayed on the monitor 13, the ultrasonic diagnostic apparatus 1 stores the log information, which includes the marker information and time information, in the storage circuitry 127. Thereafter, the ultrasonic diagnostic apparatus 1 specifies the medical image and marker information in the storage circuitry 127, based on the time information designated by the user, and causes the monitor 13 to display, based on the specified marker information, the composite image in which the marker is composited on the specified medical image.

In this manner, while the composite image is displayed, the marker and ultrasonic image are individually stored. By this configuration, at a time of giving an explanation to the subject P at a later date, the ultrasonic image, which does not include the arrow, can be displayed. In addition, when the first operator 3 or second operator 4 confirms the screen at the time of the examination, the composite image, in which the marker is composited on the ultrasonic image, can be displayed based on the time information.

Additionally, according to the modification illustrated in FIG. 14, the ultrasonic diagnostic apparatus 1 generates the second compressed image by compressing the composite image, and wirelessly transmits this second compressed image to the terminal device 2. The terminal device 2 receives the second compressed image, and causes the display circuitry 22 to display the second compressed image, such that the second compressed image is substantially synchronized with the display of the composite image on the monitor 13. Thereby, the same advantageous effects as in the flow of (4) can be obtained.

As regards the above (5) flow of sharing text information, the ultrasonic diagnostic apparatus 1, which functions as the medical diagnostic apparatus, generates a medical image, based on the output of the ultrasonic probe 11, and causes the monitor 13, which functions as the first display circuitry, to display the medical image. In addition, the ultrasonic diagnostic apparatus 1 compresses the medical image, and wirelessly transmits this first compressed image to the terminal device 2.

The terminal device 2 receives the first compressed image which is wirelessly transmitted, and causes the display circuitry 22, which functions as the second display circuitry, to display the first compressed image, such that the first compressed image is substantially synchronized with the display of the medical image on the monitor 13. In accordance with the input from the user, the terminal device 2 generates text information, and wirelessly transmits this text information to the ultrasonic diagnostic apparatus 1.

The ultrasonic diagnostic apparatus 1 receives the text information which is wirelessly transmitted from the terminal device 2, and causes the monitor 13 to display this text information together with the medical image. When both the text information and the medical image are displayed on the monitor 13, the ultrasonic diagnostic apparatus 1 generates the capture image which does not include the text information, with respect to the information in the screen of the monitor 13.

In this manner, while the ultrasonic diagnostic apparatus 1 and terminal device 2 are displaying the common medical image and compressed image thereof, the text information, which is input by the terminal device 2, is displayed on each of the terminal device 2 and ultrasonic diagnostic apparatus 1. Accordingly, based on the text information displayed on the ultrasonic diagnostic apparatus 1, even the unskilled first operator 3 can execute a proper operation, without causing anxiety to the subject P.

Furthermore, as regards the above (5) flow of sharing the text information, the ultrasonic diagnostic apparatus 1 stores the capture image and time information in the storage circuitry 127 by associating the capture image and time information. In addition, when both the text information and the medical image are being displayed on the monitor 13, the ultrasonic diagnostic apparatus 1 stores the log information, which includes the text information and time information, in the storage circuitry 127. Thereafter, the ultrasonic diagnostic apparatus 1 causes the monitor 13 to display the text information in the storage circuitry 127 together with the capture image, based on the time information designated by the user.

In this manner, while the text information and the ultrasonic image are displayed, the text information and ultrasonic image are individually stored. By this configuration, at a time of giving an explanation to the subject P at a later date, the ultrasonic image, which does not include the text information, can be displayed. In addition, when the first operator 3 or second operator 4 confirms the screen at the time of the examination, the text information together with the ultrasonic image can be displayed based on the time information.

As regards the above (6) flow of sharing the marker and text information, the ultrasonic diagnostic apparatus 1, which functions as the medical diagnostic apparatus, generates a medical image, based on the output of the ultrasonic probe 11, and causes the monitor 13, which functions as the first display circuitry, to display the medical image. In addition, the ultrasonic diagnostic apparatus 1 compresses the medical image, and wirelessly transmits this first compressed image to the terminal device 2.

The terminal device 2 receives the first compressed image which is wirelessly transmitted, and causes the display circuitry 22, which functions as the second display circuitry, to display the first compressed image, such that the first compressed image is substantially synchronized with the display of the medical image on the monitor 13, and to display the marker at a position on the first compressed image, which is designated by the user. In addition, the terminal device 2 generates text information in accordance with the input from the user, and wirelessly transmits this text information, and marker information including the position information of the marker displayed on the compressed image, to the ultrasonic diagnostic apparatus 1.

The ultrasonic diagnostic apparatus 1 receives the text information and marker information, which are wirelessly transmitted from the terminal device 2, and causes the monitor 13 to display this text information together with the medical image, and to display the marker on the medical image, based on the marker information.

In this manner, while the ultrasonic diagnostic apparatus 1 and terminal device 2 are displaying the common medical image and compressed image thereof, the marker and text information designated by the terminal device 2 are displayed on each of the terminal device 2 and ultrasonic diagnostic apparatus 1. Accordingly, based on the marker and text information displayed on the ultrasonic diagnostic apparatus 1, even the unskilled first operator 3 can execute a proper operation, without causing anxiety to the subject P.

Additionally, when the communication between the ultrasonic diagnostic apparatus 1 and terminal device 2 is executed directly without intervention of an external server, a delay in communication speed due to the external server can be prevented.

In addition, when the ultrasonic diagnostic apparatus 1 displays the text information at a position, which does not overlap the medical image, on the screen of the monitor 13, the ultrasonic diagnostic apparatus 1 can display the text information without a hindrance to diagnostic reading.

Besides, as regards the above (6) flow of sharing the marker and text information, when the marker is displayed on the medical image, the ultrasonic diagnostic apparatus 1 stores the medical image, which does not include the marker, and the time information in the storage circuitry 127 by associating the medical image and time information. In addition, when the text information, medical image and marker are being displayed on the monitor 13, the ultrasonic diagnostic apparatus 1 stores the log information, which includes the text information, marker information and time information, in the storage circuitry 127. Thereafter, the ultrasonic diagnostic apparatus 1 causes the monitor 13 to display the text information in the storage circuitry 127 together with the medical image, based on the time information designated by the user, and to display the marker on the medical image, based on the marker information in the storage circuitry 127.

In this manner, while the text information and the ultrasonic image, on which the marker is superimposed, are displayed, both the text information and marker, on the one hand, and the ultrasonic image, on the other hand, are individually stored. By this configuration, at a time of giving an explanation to the subject P at a later date, the ultrasonic image, which includes neither the text information nor the arrow, can be displayed. In addition, when the first operator 3 or second operator 4 confirms the screen at the time of the examination, the text information, together with the ultrasonic image on which the arrow is superimposed, can be displayed based on the time information.

Furthermore, when the ultrasonic diagnostic apparatus 1 displays, based on the marker information, the trace of the marker for a predetermined time, together with the marker on the medical image, an improvement in visibility of the first operator 3 and an improvement in operability of the second operator 4 can be expected.

As regards the above (7) flow of sharing the image with changed image quality, the ultrasonic diagnostic apparatus 1 receives a command signal which is wirelessly transmitted from the terminal device 2, and changes the image quality of the medical image which is being displayed on the monitor 13, based on this command signal.

For example, while the ultrasonic diagnostic apparatus 1 and terminal device 2 are displaying the common medical image and compressed image thereof, the text information, which is generated by the terminal device 2, is displayed on each of the terminal device 2 and ultrasonic diagnostic apparatus 1, and thereafter the image quality of the ultrasonic diagnostic apparatus 1 is changed. Accordingly, based on the text information displayed on the ultrasonic diagnostic apparatus 1 and the medical image after the change of the image quality, even the unskilled first operator 3 can execute a proper operation, without causing anxiety to the subject P.

Furthermore, as regards the above (7) flow of sharing the image with the changed image quality, while the text information and the ultrasonic image with the changed image quality are displayed, the text information, the information indicative of the command signal, and the ultrasonic image are individually stored. By this configuration, at a time of giving an explanation to the subject P at a later date, the ultrasonic image, which includes neither the text information nor the information indicative of the command signal, can be displayed. In addition, when the first operator 3 or second operator 4 confirms the screen at the time of the examination, both the text information and the information indicative of the command signal can be displayed together with the ultrasonic image, based on the time information.

Other Embodiments

In the meantime, the present invention is not limited to the above-described embodiment. For example, in the first embodiment, the storage circuitry 127 stores the operation screen database representing the operation screen, which is displayed on the touch panel that the input interface circuitry 21 of the terminal device 2 includes, and through which the second operator 4 operates the ultrasonic diagnostic apparatus 1 from the terminal device 2. However, the restriction to this is unnecessary. For example, the storage circuitry 127 may store an operation screen database representing an operation screen, which is displayed on the touch panel that the input interface circuitry 14 of the ultrasonic diagnostic apparatus 1 includes, and through which the first operator 3 operates the ultrasonic diagnostic apparatus 1. In this case, the system control circuitry 128 generates terminal operation screen data by processing the image data or the like, which is acquired from the operation screen database, in accordance with a command signal from the terminal device 2. Thereby, the second operator 4 can change the operation screen for operating the ultrasonic diagnostic apparatus 1, which is displayed on the touch panel which the input interface circuitry 21 of the terminal device 2 includes.

Additionally, in the first embodiment, the operation screen database includes a plurality of image data of various patterns, and additional information of the image data, the image data of the various patterns corresponding to command signals for the second operator 4 to operate the ultrasonic diagnostic apparatus 1 from the terminal device 2. However, the restriction to this is unnecessary. For example, the storage circuitry 127 may store the image data representing operation screens of various patterns corresponding to the command signals of the terminal device 2, by dividing the image data into a plurality of partial image data representing operation button images, etc. In addition, the storage circuitry 127 stores disposition information or the like, which indicates at which positions on the image, which represents the operation screen including the partial images, images represented by the partial image data are disposed. In this case, the system control circuitry 128 executes the operation screen generation function 128-1, and combines the plural partial image data, thereby generating the terminal operation screen data corresponding to the command signal.

Additionally, in the present embodiment, if the result of the comparison in step S23 of FIG. 5 indicates that Ru is not greater than Rt, the system control circuitry 128 does not change the compression ratio, and keeps the predetermined compression ratio. Besides, in the first embodiment, if the result of the comparison in step S33 of FIG. 6 indicates that Ru is not greater than Rt, the system control circuitry 128 does not change the compression ratio, and keeps the predetermined compression ratio. However, the restriction to this is unnecessary. Specifically, the system control circuitry 128 may change the preset value so that the Ru after compression becomes equal to Rt, that is, so that the preset compression ratio of image data for transfer becomes lower. Thereby, the image quality of the image represented by the image data for transfer can be made closer to the image quality of the image represented by the ultrasonic image data which the display processing circuitry 126 generates.

Additionally, in the first embodiment, the display frame of the ultrasonic image, which is generated by the display processing circuitry 126, may be generated, for example, based on image data generated by a cyclical scan on a two-dimensional region with use of a one-dimensional array probe, or may be generated based on image data generated by executing a rendering process or an MPR process on volume data which is generated by a cyclical scan on a three-dimensional region with use of a two-dimensional array probe.

The term "processor" used in the above description means, for example, a CPU (Central Processing Unit), a GPU (Graphics Processing Unit), or circuitry such as an ASIC (Application Specific Integrated Circuit), or a programmable logic device (e.g. SPLD (Simple Programmable Logic Device), CLPD (Complex Programmable Logic Device), FPGA (Field Programmable Gate Array)). The processor realizes functions by reading out and executing programs stored in the memory circuitry. In the meantime, instead of storing programs in the memory circuitry, such a configuration may be adopted that programs are directly incorporated in the circuitry in the processor. In this case, the processor realizes functions by reading out and executing programs incorporated in the circuitry in the processor. Each of the processors in the embodiment may not be configured as single circuitry for each processor. A plurality of independent circuitries may be constructed as a single processor, and the functions of the processor may be realized. Furthermore, a plurality of structural elements in FIG. 1 and FIG. 2 may be integrated in a single processor, and the functions of the processor may be realized.

The ultrasonic diagnostic system and ultrasonic diagnostic apparatus 1 in the first embodiment are examples of a medical diagnostic system and a medical diagnostic apparatus in the claims. The ultrasonic probe 11 in the first embodiment is an example of an ultrasonic probe or an X-ray detector in the claims. The ultrasonic transmission/reception circuitry 121, B mode processing circuitry 122, blood flow detection circuitry 123, volume data generation circuitry 124 and image processing circuitry 125 in the first embodiment are examples of medical image generation circuitry in the claims. The monitor 13 in the first embodiment is an example of first display circuitry in the claims. The display processing circuitry 126 and system control circuitry 128 in the first embodiment are examples of first display control circuitry in the claims. The image encoding circuitry 130 in the first embodiment is an example of compression circuitry in the claims. The communication interface circuitry 131 in the first embodiment is an example of first communication circuitry in the claims. The communication interface circuitry 23 in the first embodiment is an example of second communication circuitry in the claims. The display circuitry 22 in the first embodiment is an example of second display circuitry in the claims. The arrow ar in the first embodiment is an example of a marker in the claims. The system control circuitry 24 in the first embodiment is an example of second display control circuitry, marker information generation circuitry and text information generation circuitry in the claims. The system control circuitry 128 in the first embodiment is an example of capture image generation circuitry, medical image storing circuitry, log storing circuitry and capture image storing circuitry in the claims.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A medical diagnostic apparatus which is communicable with a terminal device, comprising:
   medical image generation circuitry configured to generate a medical image, based on an output of an ultrasonic probe or an X-ray detector;
   first display control circuitry configured to cause first display circuitry to display the medical image;
   compression circuitry configured to generate a first compressed image by compressing the medical image;
   first communication circuitry configured to wirelessly transmit the generated first compressed image to the terminal device;
   one-time password display circuitry configured to generate and update a one-time password for every communication connection request from the terminal device and to display the one-time password at a predetermined position on a screen of the first display circuitry;
   authentication circuitry which permits communication between the first communication circuitry and the terminal device, when the one-time password displayed has been input by the terminal device; and
   control circuitry, wherein,
   if marker information including position information indicative of a position on the first compressed image, which position is designated by a user, is generated and wirelessly transmitted from the terminal device while the first compressed image is being displayed on the terminal device such that the first compressed image is substantially synchronized with the display of the medical image on the first display circuitry, the first communication circuitry is configured to receive the marker information which is wirelessly transmitted from the terminal device, the first display control circuitry is configured to cause the first display circuitry to display a composite image in which a marker is composited on the medical image, based on the marker information, and the control circuitry is configured to store in storage circuitry the medical image which constitutes the composite image, in accordance with a storage request that is accepted while the composite image is being displayed on the first display circuitry.

2. The medical diagnostic apparatus of claim 1, wherein the compression circuitry is configured to generate a second compressed image by compressing the composite image, the first communication circuitry is configured to wirelessly transmit the second compressed image to the terminal device, and the terminal device is configured to receive the second compressed image which is wirelessly transmitted from the medical diagnostic apparatus, and configured to display the second compressed image such that the second compressed image is substantially synchronized with the display of the composite image on the first display circuitry.

3. The medical diagnostic apparatus of claim 1, wherein the terminal device is configured to wirelessly transmit, upon accepting an input of the storage request, a control signal to the medical diagnostic apparatus in accordance with the accepted storage request, the first communication circuitry is configured to receive the control signal which is wirelessly transmitted from the terminal device, and the control circuitry is configured to store in the storage circuitry the medical image which constitutes the composite image, in accordance with the received control signal.

4. The medical diagnostic apparatus of claim 1, further comprising input circuitry configured to send, upon accepting an input of the storage request, a control signal to the control circuitry in accordance with the accepted storage request, wherein the control circuitry is configured to store in the storage circuitry the medical image which constitutes the composite image, in accordance with the sent control signal.

5. The medical diagnostic apparatus of claim 1, wherein the terminal device is configured to generate and wirelessly transmit text information in accordance with an input from the user, the first communication circuitry is configured to receive the text information which is wirelessly transmitted from the terminal device, and the first display control circuitry is configured to cause the first display circuitry to display the text information together with the composite image.

6. The medical diagnostic apparatus of claim 1, further comprising:

medical image storing circuitry configured to store in the storage circuitry the medical image, which constitutes the composite image, and time information by associating the medical image and the time information, when the composite image is being displayed; and log storing circuitry configured to store in the storage circuitry log information including the marker information and the time information, when the composite image is being displayed, wherein the first display control circuitry is configured to specify the medical image and the marker information in the storage circuitry, based on the time information designated by the user, and configured to display a composite image in which the marker is composited on the specified medical image, based on the specified marker information.

7. The medical diagnostic apparatus of claim 1, wherein the first display control circuitry is configured to display a trace of the marker in the composite image for a predetermined time, based on the marker information.

8. A medical diagnostic apparatus which is communicable with a terminal device, comprising:

medical image generation circuitry configured to generate a medical image, based on an output of an ultrasonic probe or an X-ray detector;

first display control circuitry configured to cause first display circuitry to display the medical image;

compression circuitry configured to generate a first compressed image by compressing the medical image;

first communication circuitry configured to wirelessly transmit the first compressed image to the terminal device;

capture image generation circuitry, and storage circuitry, wherein the first communication circuitry is configured to receive text information which is generated and wirelessly transmitted by the terminal device which displays the first compressed image, the first display control circuitry is configured to cause the first display circuitry to display the text information together with the medical image, the capture image generation circuitry is configured to generate a capture image which does not include the text information with respect to information in a screen of the first display circuitry, when both the text information and the medical image are being displayed on the first display circuitry; and control circuitry configured to store the capture image in the storage circuitry in accordance with a storage request which is accepted when both the text information and the medical image are being displayed on the first display circuitry.

9. The medical diagnostic apparatus of claim 8, wherein the terminal device is configured to wirelessly transmit, upon accepting an input of the storage request, a control signal to the medical diagnostic apparatus in accordance with the accepted storage request, the first communication circuitry is configured to receive the control signal which is wirelessly transmitted from the terminal device, and the control circuitry is configured to store the capture image in the storage circuitry in accordance with the received control signal.

10. The medical diagnostic apparatus of claim 8, further comprising input circuitry configured to send, upon accepting an input of the storage request, a control signal to the control circuitry in accordance with the accepted storage request, wherein the control circuitry is configured to store the capture image in the storage circuitry in accordance with the sent control signal.

11. The medical diagnostic apparatus of claim 8, wherein the first display control circuitry is configured to display the text information at a position, which does not overlap the medical image, on the screen of the first display circuitry.

12. The medical diagnostic apparatus of claim 8, further comprising:
   capture image storing circuitry configured to store in storage circuitry the capture image and time information by associating the capture image and the time information; and
   log storing circuitry configured to store in the storage circuitry log information including the text information and the time information, when both the text information and the medical image are being displayed on the first display circuitry,
   wherein the first display control circuitry is configured to cause the first display circuitry to display the text information in the storage circuitry, together with the capture image, based on the time information designated by the user.

13. The medical diagnostic apparatus of claim 8, wherein the first communication circuitry is configured to receive a command signal which is wirelessly transmitted from the terminal device, and
   the first display control circuitry is configured to change, based on the command signal, an image quality of the medical image which is being displayed on the first display circuitry.

14. A medical diagnostic system comprising a medical diagnostic apparatus and a terminal device,
   the medical diagnostic apparatus comprising:
      medical image generation circuitry configured to generate a medical image, based on an output of an ultrasonic probe or an X-ray detector;
      first display control circuitry configured to cause first display circuitry to display the medical image;
      compression circuitry configured to generate a first compressed image by compressing the medical image;
      first communication circuitry configured to wirelessly transmit the first compressed image to the terminal device;
      one-time password display circuitry configured to generate and update a one-time password for every communication connection request from the terminal device and to display the one-time password at a predetermined position on a screen of the first display circuitry;
      authentication circuitry which permits communication between the first communication circuitry and the terminal device, when the one-time password displayed has been input by the terminal device; and
      control circuitry, and
   the terminal device comprising:
      second communication circuitry configured to receive the first compressed image which is wirelessly transmitted from the medical diagnostic apparatus;
      second display control circuitry configured to cause second display circuitry to display the first compressed image such that the first compressed image is substantially synchronized with the display of the medical image on the first display circuitry; and
      marker information generation circuitry configured to generate marker information including position information indicative of a position on the first compressed image, in accordance with an input from a user,
   wherein the second communication circuitry is configured to wirelessly transmit the marker information to the medical diagnostic apparatus,
   the first communication circuitry is configured to receive the marker information which is wirelessly transmitted from the terminal device,
   the first display control circuitry is configured to cause the first display circuitry to display a composite image in which a marker is composited on the medical image, based on the marker information, and
   the control circuitry is configured to store in storage circuitry the medical image which constitutes the composite image, in accordance with a storage request that is accepted while the composite image is being displayed on the first display circuitry.

15. The medical diagnostic system of claim 14, wherein the compression circuitry is configured to generate a second compressed image by compressing the composite image,
   the first communication circuitry is configured to wirelessly transmit the second compressed image to the terminal device,
   the second communication circuitry is configured to receive the second compressed image which is wirelessly transmitted from the medical diagnostic apparatus, and
   the second display control circuitry is configured to cause the second display circuitry to display the second compressed image such that the second compressed image is substantially synchronized with the display of the composite image on the first display circuitry.

16. The medical diagnostic system of claim 14, wherein the terminal device includes input circuitry configured to send, upon accepting an input of the storage request, a control signal to the second communication circuitry in accordance with the accepted storage request,
   the second communication circuitry is configured to wirelessly transmit the sent control signal to the medical diagnostic apparatus,
   the first communication circuitry is configured to receive the control signal which is wirelessly transmitted from the second communication circuitry, and
   the control circuitry is configured to store in the storage circuitry the medical image which constitutes the composite image, in accordance with the received control signal.

17. The medical diagnostic system of claim 14, wherein the medical diagnostic apparatus includes input circuitry configured to send, upon accepting the storage request, a control signal to the control circuitry in accordance with the accepted storage request, and
   the control circuitry is configured to store in the storage circuitry the medical image which constitutes the composite image, in accordance with the sent control signal.

18. The medical diagnostic system of claim 14, wherein the terminal device further comprises text information generation circuitry configured to generate text information in accordance with an input from the user,
   wherein the second communication circuitry is configured to wirelessly transmit the text information to the medical diagnostic apparatus,
   the first communication circuitry is configured to receive the text information which is wirelessly transmitted from the terminal device, and the first display control circuitry is configured to cause the first display circuitry to display the text information together with the medical image.

* * * * *